US011168349B2

(12) United States Patent
Soya et al.

(10) Patent No.: US 11,168,349 B2
(45) Date of Patent: Nov. 9, 2021

(54) METHOD FOR MEASURING GLYCATED HEMOGLOBIN

(71) Applicant: Hitachi Chemical Diagnostics Systems Co., Ltd., Tokyo (JP)

(72) Inventors: Haruyo Soya, Sunto-gun (JP); Yuki Katayama, Sunto-gun (JP); Noriyuki Ogawa, Sunto-gun (JP)

(73) Assignee: Hitachi Chemical Diagnostics Systems Co., Ltd., Tokyo (JP)

( * ) Notice: Subject to any disclaimer, the term of this patent is extended or adjusted under 35 U.S.C. 154(b) by 103 days.

(21) Appl. No.: 16/319,853

(22) PCT Filed: Jul. 28, 2017

(86) PCT No.: PCT/JP2017/027442
§ 371 (c)(1),
(2) Date: Jan. 23, 2019

(87) PCT Pub. No.: WO2018/021530
PCT Pub. Date: Feb. 1, 2018

(65) Prior Publication Data
US 2019/0249222 A1    Aug. 15, 2019

(30) Foreign Application Priority Data
Jul. 29, 2016 (JP) .............................. JP2016-150498

(51) Int. Cl.
*C12Q 1/28* (2006.01)
*G01N 33/72* (2006.01)
*C12Q 1/26* (2006.01)

(52) U.S. Cl.
CPC ................. *C12Q 1/28* (2013.01); *C12Q 1/26* (2013.01); *G01N 33/72* (2013.01)

(58) Field of Classification Search
None
See application file for complete search history.

(56) References Cited

U.S. PATENT DOCUMENTS

| 2007/0154976 | A1 | 7/2007 | Taniguchi et al. |
| 2007/0224685 | A1 | 9/2007 | Kouzuma et al. |
| 2015/0118700 | A1 | 4/2015 | Ichiyanagi et al. |
| 2016/0123999 | A1 | 5/2016 | Ogawa et al. |
| 2016/0138073 | A1 | 5/2016 | Ogawa et al. |
| 2016/0251695 | A1 | 9/2016 | Masakari et al. |

FOREIGN PATENT DOCUMENTS

| CN | 101490558 A | 7/2009 | | |
| CN | 103069003 A | 4/2013 | | |
| CN | 103124793 A | 5/2013 | | |
| CN | 104313121 A | 1/2015 | | |
| EP | 2 722 396 | 4/2014 | | |
| EP | 3 020 825 | 5/2016 | | |
| JP | 2001-095598 | 4/2001 | | |
| WO | 2005/049858 | 6/2005 | | |
| WO | 2006/013921 | 2/2006 | | |
| WO | 2008/108385 | 9/2008 | | |
| WO | 2013/162035 | 10/2013 | | |
| WO | 2015/005257 | 1/2015 | | |
| WO | 2015/005258 | 1/2015 | | |
| WO | 2015/060429 | 4/2015 | | |
| WO | WO-2015060429 A1 | * | 4/2015 | ............... C12Q 1/28 |
| WO | WO-2015163384 A1 | * | 10/2015 | ........... G01N 33/723 |

OTHER PUBLICATIONS

Davis et al., "A High-performance Liquid Chromatography Method for Hemoglobin A1c", Diabetes, vol. 27, No. 2 (1978) 102-7.
Finke et al., "Preparation of a Candidate Primary Reference Material for the International Standardisation of HbA1c Determinations", Clin. Chem. Lab. Med., vol. 36, No. 5 (1998) 299-308.
Katayama et al., ""Tina-quant HbA1c", a homogenous immunoturbidimetric method for Hemoglobin A1c", Jap. J. Clin. Lab. Automat., vol. 18, No. 4 (1993) 620.
Supplementary European Search Report dated Apr. 9, 2020.
International Search Report (dated Sep. 12, 2017).
Zhou et al., "Standardization of glycated hemoglobin and the development of its detection technology," Progress in Biochemistry and Biophysics, 42 (5): 443-456 (2015) (see English abstract).
Office Action issued in related Chinese Patent Application No. 201780045924.5 dated Jul. 15, 2021 (partial English translation).

* cited by examiner

*Primary Examiner* — Michelle F. Paguio Frising
(74) *Attorney, Agent, or Firm* — Morgan, Lewis & Bockius LLP

(57) ABSTRACT

A method is provided for measuring glycated hemoglobin in a hemoglobin-containing sample which comprises reacting glycated hemoglobin in the hemoglobin-containing sample with an enzyme that catalyzes a reaction of oxidizing the glycated hemoglobin to generate hydrogen peroxide, in the presence of at least one anionic surfactant selected from the group consisting of N-acyl taurine in which a hydrogen atom of the amino group may be substituted with a substituent, alkyl sulfoacetic acid, polyoxyethylene alkyl ether acetic acid, N-acyl amino acid in which a hydrogen atom of the amino group may be substituted with a substituent, polyoxyethylene alkyl ether phosphoric acid, polyoxyethylene polycyclic phenyl ether phosphoric acid, alkyl phosphoric acid, and salts thereof, to generate hydrogen peroxide, and measuring the generated hydrogen peroxide.

7 Claims, 1 Drawing Sheet
Specification includes a Sequence Listing.

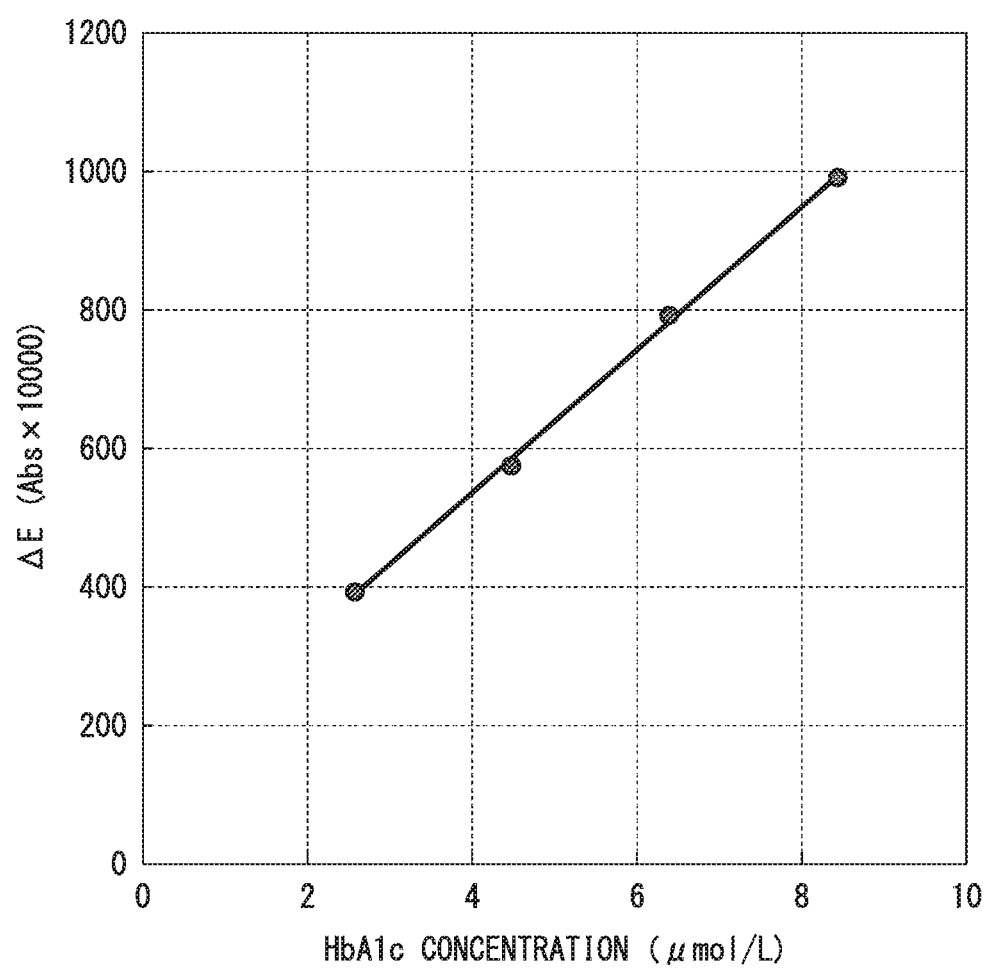

SEQUENCE LISTING

<160> NUMBER OF SEQ ID NOS: 10

<210> SEQ ID NO 1
<211> LENGTH: 1317
<212> TYPE: DNA
<213> ORGANISM: Artificial Sequence
<220> FEATURE:
<223> OTHER INFORMATION: FPOX-42

<400> SEQUENCE: 1

```
atggcgcccc gagccaacac caaaatcatc gtcgtcggcg gcggcggcac aatgggctcg      60
tcgacagccc tacacctcct gcgcgccggc tacacgccgt ccaacatcac agtgctcgac     120
acgtacccta tcccttccgc acagtctgca ggctacgacc tgaacaagat cttcggcatc     180
tcaggcgcga acaagcatga cttacaactc tcgcttgagg cgttcgacat gtggaaaaat     240
gatcctctat tcaagccgtt tttccacaat gttggacaga tggacgtctc ttcaacagaa     300
```

```
gaaggcatca aacgccttcg ccgcagatac cagtctcttc tccgcgcagg cattgggctc    360
gagaagacga atttcctgct ggaaagtgaa gacgagatcc tggctaaagc gccgcatttc    420
acgcgggagc agattaaagg ctggaaaggg ctgttctgtg gcgacggcgg ttggctcgct    480
gcagccaaag ccatcaatgc catcgggcag ttcctcaagg aacagggcgt caagtttgga    540
tttggcgagg ccggcacgtt caaaaagcca ctcttcgccg atgccgacga agacgtgc     600 atcggcgtcg aaactgtaga cggcacaaaa tactacgccg acaaggtcgt tctagcagct    660
ggtgcctgga gttcgacgtt ggtcgatctg gaggagcagt gcgtttcaaa ggcctgggtc    720
tttgcccaca tccaactgac gcccgctgaa gcagccgcgt acaagaacac tcctgttata    780
tacgacggtg actatgggtt tttcattgag ccggacgaga acggcatcat aaaagtctgc    840
gacgaattcc ctggcttcac gcacttcaag atgcaccagc cgtacggctc accggtgccc    900
aaattgatct ctgtgcctcg ctcccatgcg aagcacccca cagatacata cccgcacgcg    960
tcggaggtca ccatcaaaaa ggctatcaac cggttcctgc cgaggttcaa tgacaaggaa   1020
ctgtttaaca gggccatgtg ctggtgcacc gataccgcgg atagcaatct gcttgtttgt   1080
gagcatccac gctggaaggg gttttatctt gcaacagggg acagcgggca ttcgttcaag   1140
ttgctgccga atattggaaa gcacgttgtc gagttattgg aggggaggct ggaaagtgtg   1200
tttaaggatg cttggagtgt gaggcctggc agtggggatg cattaaagag tagacgggct   1260
gcgcctgcga aggacctggc ggatatgccg gggtggagga atgaggcaaa gatgtag      1317
```

<210> SEQ ID NO 2
<211> LENGTH: 31
<212> TYPE: DNA
<213> ORGANISM: Artificial Sequence
<220> FEATURE:
<223> OTHER INFORMATION: FPOX-42 F342V-F

<400> SEQUENCE: 2

```
gaggttcaat gacaaggaac tggtgaacag g                                    31
```

<210> SEQ ID NO 3
<211> LENGTH: 30
<212> TYPE: DNA
<213> ORGANISM: Artificial Sequence
<220> FEATURE:
<223> OTHER INFORMATION: FPOX-42 F342V-R

<400> SEQUENCE: 3

```
gcaccagcac atggccctgt tcaccagttc                                      30
```

<210> SEQ ID NO 4
<211> LENGTH: 1317
<212> TYPE: DNA
<213> ORGANISM: Artificial Sequence
<220> FEATURE:
<223> OTHER INFORMATION: FPOX-47

<400> SEQUENCE: 4

```
atggcgcccc gagccaacac caaaatcatc gtcgtcggcg gcggcggcac aatgggctcg     60
tcgacagccc tacacctcct gcgcgccggc tacacgccgt ccaacatcac agtgctcgac    120
acgtacccta tcccttccgc acagtctgca ggctacgacc tgaacaagat cttcggcatc    180
tcaggcgcga caagcatga cttacaactc tcgcttgagg cgttcgacat gtggaaaaat    240
gatcctctat tcaagccgtt tttccacaat gttggacaga tggacgtctc ttcaacagaa   300
```

```
gaaggcatca aacgccttcg ccgcagatac cagtctcttc tccgcgcagg cattgggctc      360
gagaagacga atttcctgct ggaaagtgaa gacgagatcc tggctaaagc gccgcatttc      420
acgcgggagc agattaaagg ctggaaaggg ctgttctgtg gcgacggcgg ttggctcgct      480
gcagccaaag ccatcaatgc catcgggcag ttcctcaagg aacagggcgt caagtttgga      540
tttggcgagg ccggcacgtt caaaaagcca ctcttcgccg atgccgacga aagacgtgc       600 atcggcgtcg aaactgtaga cggcacaaaa tactacgccg acaaggtcgt tctagcagct      660
ggtgcctgga gttcgacgtt ggtcgatctg gaggagcagt gcgtttcaaa ggcctgggtc      720
tttgcccaca tccaactgac gcccgctgaa gcagccgcgt acaagaacac tcctgttata      780
tacgacggtg actatgggtt tttcattgag ccggacgaga acggcatcat aaaagtctgc      840
gacgaattcc ctggcttcac gcacttcaag atgcaccagc cgtacggctc accggtgccc      900
aaattgatct ctgtgcctcg ctcccatgcg aagcacccca cagatacata cccgcacgcg      960
tcggaggtca ccatcaaaaa ggctatcaac cggttcctgc cgaggttcaa tgacaaggaa      1020
ctggtgaaca gggccatgtg ctggtgcacc gataccgcgg atagcaatct gcttgtttgt      1080
gagcatccac gctggaaggg gttttatctt gcaacagggg acagcgggca ttcgttcaag      1140
ttgctgccga atattggaaa gcacgttgtc gagttattgg aggggaggct ggaaagtgtg      1200
tttaaggatg cttggaggtg gaggcctggc agtggggatg cattaaagag tagacgggct      1260
gcgcctgcga aggacctggc ggatatgccg gggtggagga tgaggcaaa gatgtag          1317
```

<210> SEQ ID NO 5
<211> LENGTH: 21
<212> TYPE: DNA
<213> ORGANISM: Artificial Sequence
<220> FEATURE:
<223> OTHER INFORMATION: pTrc-F

<400> SEQUENCE: 5
caattaatca tccggctcgt a                                                 21

<210> SEQ ID NO 6
<211> LENGTH: 20
<212> TYPE: DNA
<213> ORGANISM: Artificial Sequence
<220> FEATURE:
<223> OTHER INFORMATION: pTrc-R

<400> SEQUENCE: 6
cttctgagtt cggcatgggg                                                   20

<210> SEQ ID NO 7
<211> LENGTH: 39
<212> TYPE: DNA
<213> ORGANISM: Artificial Sequence
<220> FEATURE:
<223> OTHER INFORMATION: FPOX-47fc3-R

<400> SEQUENCE: 7
atgggatccc tactcattcc tccaccccgg catatccgc                              39

<210> SEQ ID NO 8
<211> LENGTH: 1308
<212> TYPE: DNA
<213> ORGANISM: Artificial Sequence
<220> FEATURE:
<223> OTHER INFORMATION: FPOX-47fc3

<400> SEQUENCE: 8

```
atggcgcccc gagccaacac caaaatcatc gtcgtcggcg gcggcggcac aatgggctcg      60
tcgacagccc tacacctcct gcgcgccggc tacacgccgt ccaacatcac agtgctcgac     120
acgtacccta tcccttccgc acagtctgca ggctacgacc tgaacaagat cttcggcatc     180
tcaggcgcga caagcatga cttacaactc tcgcttgagg cgttcgacat gtggaaaaat     240
gatcctctat tcaagccgtt tttccacaat gttggacaga tggacgtctc ttcaacagaa     300
gaaggcatca aacgccttcg ccgcagatac cagtctcttc ccgcgcagg cattgggctc     360
gagaagacga atttcctgct ggaaagtgaa gacgagatcc tggctaaagc gccgcatttc     420
acgcgggagc agattaaagg ctggaaaggg ctgttctgtg cgacggcgg ttggctcgct     480
gcagccaaag ccatcaatgc catcgggcag ttcctcaagg aacagggcgt caagtttgga     540
tttggcgagg ccggcacgtt caaaaagcca ctcttcgccg atgccgacga aagacgtgc      600
atcggcgtcg aaactgtaga cggcacaaaa tactacgccg acaaggtcgt tctagcagct     660
ggtgcctgga gttcgacgtt ggtcgatctg gaggagcagt gcgtttcaaa ggcctgggtc     720
tttgcccaca tccaactgac gcccgctgaa gcagccgcgt acaagaacac tcctgttata     780
tacgacggtg actatgggtt tttcattgag ccggacgaga acggcatcat aaaagtctgc     840
gacgaattcc ctggcttcac gcacttcaag atgcaccagc cgtacggctc accggtgccc     900
aaattgatct ctgtgcctcg ctcccatgcg aagcacccca cagatacata cccgcacgcg     960
tcggaggtca ccatcaaaaa ggctatcaac cggttcctgc cgaggttcaa tgacaaggaa    1020
ctggtgaaca gggccatgtg ctggtgcacc gataccgcgg atagcaatct gcttgtttgt    1080
gagcatccac gctggaaggg gttttatctt gcaacagggg acagcgggca ttcgttcaag    1140
ttgctgccga atattggaaa gcacgttgtc gagttattgg aggggaggct ggaaagtgtg    1200
tttaaggatg cttggaggtg gaggcctggc agtggggatg cattaaagag tagacgggct    1260
gcgcctgcga aggacctggc ggatatgccg gggtggagga atgagtag              1308
```

<210> SEQ ID NO 9
<211> LENGTH: 438
<212> TYPE: PRT
<213> ORGANISM: Artificial Sequence
<220> FEATURE:
<223> OTHER INFORMATION: FPOX-47

<400> SEQUENCE: 9

```
Met Ala Pro Arg Ala Asn Thr Lys Ile Ile Val Val Gly Gly Gly Gly
1               5                   10                  15

Thr Met Gly Ser Ser Thr Ala Leu His Leu Leu Arg Ala Gly Tyr Thr
                20                  25                  30

Pro Ser Asn Ile Thr Val Leu Asp Thr Tyr Pro Ile Pro Ser Ala Gln
            35                  40                  45

Ser Ala Gly Tyr Asp Leu Asn Lys Ile Phe Gly Ile Ser Gly Ala Asn
        50                  55                  60

Lys His Asp Leu Gln Leu Ser Leu Glu Ala Phe Asp Met Trp Lys Asn
65                  70                  75                  80

Asp Pro Leu Phe Lys Pro Phe His Asn Val Gly Gln Met Asp Val
                85                  90                  95

Ser Ser Thr Glu Glu Gly Ile Lys Arg Leu Arg Arg Tyr Gln Ser
                100                 105                 110

Leu Leu Arg Ala Gly Ile Gly Leu Glu Lys Thr Asn Phe Leu Leu Glu
            115                 120                 125
```

Ser Glu Asp Glu Ile Leu Ala Lys Ala Pro His Phe Thr Arg Glu Gln
130                 135                 140

Ile Lys Gly Trp Lys Gly Leu Phe Cys Gly Asp Gly Gly Trp Leu Ala
145                 150                 155                 160

Ala Ala Lys Ala Ile Asn Ala Ile Gly Gln Phe Leu Lys Glu Gln Gly
                165                 170                 175

Val Lys Phe Gly Phe Gly Glu Ala Gly Thr Phe Lys Lys Pro Leu Phe
                180                 185                 190

Ala Asp Ala Asp Glu Lys Thr Cys Ile Gly Val Glu Thr Val Asp Gly
                195                 200                 205

Thr Lys Tyr Tyr Ala Asp Lys Val Val Leu Ala Ala Gly Ala Trp Ser
210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
                245                 250                 255

Thr Pro Val Ile Tyr Asp Gly Asp Tyr Gly Phe Phe Ile Glu Pro Asp
                260                 265                 270

Glu Asn Gly Ile Ile Lys Val Cys Asp Glu Phe Pro Gly Phe Thr His
                275                 280                 285

Phe Lys Met His Gln Pro Tyr Gly Ser Pro Val Pro Lys Leu Ile Ser
290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335

Asn Asp Lys Glu Leu Val Asn Arg Ala Met Cys Trp Cys Thr Asp Thr
                340                 345                 350

Ala Asp Ser Asn Leu Leu Val Cys Glu His Pro Arg Trp Lys Gly Phe
                355                 360                 365

Tyr Leu Ala Thr Gly Asp Ser Gly His Ser Phe Lys Leu Leu Pro Asn
370                 375                 380

Ile Gly Lys His Val Val Glu Leu Leu Glu Gly Arg Leu Glu Ser Val
385                 390                 395                 400

Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
                420                 425                 430

Arg Asn Glu Ala Lys Met
        435

<210> SEQ ID NO 10
<211> LENGTH: 435
<212> TYPE: PRT
<213> ORGANISM: Artificial Sequence
<220> FEATURE:
<223> OTHER INFORMATION: FPOX-47fc3

<400> SEQUENCE: 10

Met Ala Pro Arg Ala Asn Thr Lys Ile Ile Val Val Gly Gly Gly Gly
1               5                   10                  15

Thr Met Gly Ser Ser Thr Ala Leu His Leu Leu Arg Ala Gly Tyr Thr
                20                  25                  30

Pro Ser Asn Ile Thr Val Leu Asp Thr Tyr Pro Ile Pro Ser Ala Gln
                35                  40                  45

```
Ser Ala Gly Tyr Asp Leu Asn Lys Ile Phe Gly Ile Ser Gly Ala Asn
    50                  55                  60

Lys His Asp Leu Gln Leu Ser Leu Glu Ala Phe Asp Met Trp Lys Asn
 65                  70                  75                  80

Asp Pro Leu Phe Lys Pro Phe Phe His Asn Val Gly Gln Met Asp Val
                 85                  90                  95

Ser Ser Thr Glu Glu Gly Ile Lys Arg Leu Arg Arg Tyr Gln Ser
            100                 105                 110

Leu Leu Arg Ala Gly Ile Gly Leu Glu Lys Thr Asn Phe Leu Leu Glu
        115                 120                 125

Ser Glu Asp Glu Ile Leu Ala Lys Ala Pro His Phe Thr Arg Glu Gln
    130                 135                 140

Ile Lys Gly Trp Lys Gly Leu Phe Cys Gly Asp Gly Gly Trp Leu Ala
145                 150                 155                 160

Ala Ala Lys Ala Ile Asn Ala Ile Gly Gln Phe Leu Lys Glu Gln Gly
                165                 170                 175

Val Lys Phe Gly Phe Gly Glu Ala Gly Thr Phe Lys Lys Pro Leu Phe
        180                 185                 190

Ala Asp Ala Asp Glu Lys Thr Cys Ile Gly Val Glu Thr Val Asp Gly
    195                 200                 205

Thr Lys Tyr Tyr Ala Asp Lys Val Val Leu Ala Ala Gly Ala Trp Ser
    210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
                245                 250                 255

Thr Pro Val Ile Tyr Asp Gly Asp Tyr Gly Phe Phe Ile Glu Pro Asp
            260                 265                 270

Glu Asn Gly Ile Ile Lys Val Cys Asp Glu Phe Pro Gly Phe Thr His
        275                 280                 285

Phe Lys Met His Gln Pro Tyr Gly Ser Pro Val Pro Lys Leu Ile Ser
290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335

Asn Asp Lys Glu Leu Val Asn Arg Ala Met Cys Trp Cys Thr Asp Thr
        340                 345                 350

Ala Asp Ser Asn Leu Leu Val Cys Glu His Pro Arg Trp Lys Gly Phe
    355                 360                 365

Tyr Leu Ala Thr Gly Asp Ser Gly His Ser Phe Lys Leu Leu Pro Asn
    370                 375                 380

Ile Gly Lys His Val Val Glu Leu Leu Glu Gly Arg Leu Glu Ser Val
385                 390                 395                 400

Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
        420                 425                 430

Arg Asn Glu
        435
```

METHOD FOR MEASURING GLYCATED HEMOGLOBIN

TECHNICAL FIELD

[0001]
The present invention relates to a method, a reagent and a kit for measuring glycated hemoglobin in a sample.

This application is a National Phase of International Application No. PCT/JP2017/027442 filed Jul. 28, 2017, which in turn claims priority on Japanese Patent Application No. 2016-150498, filed on Jul. 29, 2016, the content of which are incorporated herein by reference.

BACKGROUND ART

A glycated protein is contained in biological samples such as body fluid and hair, and body fluid includes blood in a living body, and such. The concentration of a glycated protein present in blood depends on the concentration of saccharides such as glucose dissolved in serum. In the field of clinical diagnosis, measurement of the concentration of hemoglobin A1c (hereinafter referred to as HbA1c), which is a glycated protein in blood, is used for diagnosis and monitoring of diabetes (see Non-Patent Document 1). Hemoglobin is a hemoprotein consisting of two of each of two types of subunits, the α chain and the 13 chain, and has a molecular weight of 64,000. HbA1c is defined as a hemoglobin in which, in particular, an N-terminal valine residue of β chain is glycated. As a method for measuring HbA1c, an instrumental analytical method using high-performance liquid chromatography (HPLC) (see Non-Patent Document 2), an immunoassay method using an antigen-antibody reaction (Non-Patent Document 3), and the like are known.

In recent years, the development of an enzymatic measurement method for HbA1c, which is applicable to an automatic analyzer with versatility and also easy to operate, is in progress, and various methods are being reported. Enzymatic measurement methods for HbA1c which have been reported so far are mainly methods using both of a protease and a glycated peptide oxidase. That is, there is a method for measuring HbA1c in a sample in which a protease is allowed to act on HbA1c in blood cells so as to generate a fructosyl dipeptide (Fru-Val-His), which is a glycated peptide, a fructosyl peptide oxidase is allowed to act on the generated fructosyl dipeptide so as to generate hydrogen peroxide, and the generated hydrogen peroxide is measured (see Patent Document 1); and a method for measuring HbA1c in a sample in which a protease is allowed to act on HbA1c in blood cells so as to generate a fructosyl hexapeptide (Fru-Val-His-Leu-Thr-Pro-Glu), which is a glycated peptide, a fructosyl hexapeptide oxidase is allowed to act on the generated fructosyl hexapeptide so as to generate hydrogen peroxide, and the generated hydrogen peroxide is measured (see Patent Documents 2 to 4). On the other hand, a method for measuring glycated hemoglobin in a sample by using an enzyme that catalyzes a reaction of oxidizing glycated hemoglobin to generate hydrogen peroxide without using a protease is also known (see Patent Documents 4 to 6).

In addition, a method for measuring an HbA1c concentration and an HbA1c concentration ratio characterized by performing hemoglobin measurement in a sample containing hemoglobin pretreated with at least an anionic surfactant, and further performing measurement of the HbA1c concentration by allowing a proteolytic enzyme that generates fructosyl valyl histidine to act on a reaction solution for hemoglobin measurement has been reported (see Patent Document 7).

PRIOR ART DOCUMENTS

Patent Documents

[Patent Document 1] Japanese Unexamined Patent Application, First Publication No. 2001-95598
[Patent Document 2] PCT International Publication No. WO2008/108385
[Patent Document 3] PCT International Publication No. WO2013/162035
[Patent Document 4] PCT International Publication No. WO2015/005258
[Patent Document 5] PCT International Publication No. WO2015/005257
[Patent Document 6] PCT International Publication No. WO2015/060429
[Patent Document 7] PCT International Publication No. WO2005/049858

Non-Patent Literature

[Non-Patent Document 1] Clin Chem Lab Med, Vol. 36, pp. 299 to 308 (1998).
[Non-Patent Document 2] Diabetes, Vol. 27, No. 2, pp. 102 to 107 (1978).
[Non-Patent Document 3] Japanese Journal of Clinical Laboratory Automation, Vol. 18, No. 4, p. 620 (1993).

SUMMARY OF INVENTION

Problems to be Solved by the Invention

The methods in the related art, using an enzyme that catalyzes a reaction of oxidizing glycated hemoglobin to generate hydrogen peroxide without using a protease, have a problem of exhibiting insufficient sensitivity.

Accordingly, an object of the present invention is to provide a method, a reagent, and a kit for measuring glycated hemoglobin in a sample in a simple and highly sensitive manner by using an enzyme that catalyzes a reaction of oxidizing glycated hemoglobin to generate hydrogen peroxide.

Means for Solving the Problems

The present inventors have conducted intensive studies to solve such a problem, and have found that glycated hemoglobin in a sample containing hemoglobin can be measured in a simple and highly sensitive manner by reacting glycated hemoglobin in a hemoglobin-containing sample with an enzyme that catalyzes a reaction of oxidizing glycated hemoglobin to generate hydrogen peroxide in the presence of a specific anionic surfactant, thus completing the present invention.

That is, the present invention relates to the following [1] to [15].

[1] A method for measuring glycated hemoglobin in a hemoglobin-containing sample, comprising:
reacting glycated hemoglobin in the hemoglobin-containing sample with an enzyme that catalyzes a reaction of oxidizing the glycated hemoglobin to generate hydrogen peroxide, in the presence of at least one anionic surfactant selected from the group consisting of N-acyl taurine in which a hydrogen atom of the amino group may be substituted with a substituent, alkyl sulfoacetic acid, polyoxyethylene alkyl ether acetic acid, N-acyl amino acid in which a hydrogen atom of the amino group may be substituted with a substituent, polyoxyethylene alkyl ether phosphoric acid, polyoxyethylene polycyclic phenyl ether phosphoric acid, alkyl phosphoric acid, and salts thereof, to generate hydrogen peroxide; and measuring the generated hydrogen peroxide.

[2] The method according to [1],
wherein the measurement of the hydrogen peroxide is carried out with a reagent for measuring hydrogen peroxide.

[3] The method according to [2],
wherein the reagent for measuring hydrogen peroxide is a reagent containing a peroxidase and a leuco-type chromogen.

[4] The method according to [3],
wherein the leuco-type chromogen is a phenothiazine-based chromogen.

[5] The method according to [4],
wherein the phenothiazine-based chromogen is 10-(carboxymethylaminocarbonyl)-3,7-bis(dimethylamino)phenothiazine or a salt thereof.

[6] A reagent for measuring glycated hemoglobin in a hemoglobin-containing sample, comprising:

an enzyme that catalyzes a reaction of oxidizing glycated hemoglobin to generate hydrogen peroxide; and at least one anionic surfactant selected from the group consisting of N-acyl taurine in which a hydrogen atom of the amino group may be substituted with a substituent, alkyl sulfoacetic acid, polyoxyethylene alkyl ether acetic acid, N-acyl amino acid in which a hydrogen atom of the amino group may be substituted with a substituent, polyoxyethylene alkyl ether phosphoric acid, polyoxyethylene polycyclic phenyl ether phosphoric acid, alkyl phosphoric acid, and salts thereof.

[7] The reagent according to [6], further comprising:
a reagent for measuring hydrogen peroxide.

[8] The reagent according to [7],
wherein the reagent for measuring hydrogen peroxide is a reagent containing a peroxidase and a leuco-type chromogen.

[9] The reagent according to [8],
wherein the leuco-type chromogen is a phenothiazine-based chromogen.

[10] The reagent according to [9],
wherein the phenothiazine-based chromogen is 10-(carboxymethylaminocarbonyl)-3,7-bis(dimethylamino)phenothiazine or a salt thereof.

[11] A kit for measuring glycated hemoglobin in a hemoglobin-containing sample, comprising:

a first reagent which comprises at least one anionic surfactant selected from the group consisting of N-acyl taurine in which a hydrogen atom of the amino group may be substituted with a substituent, alkyl sulfoacetic acid, polyoxyethylene alkyl ether acetic acid, N-acyl amino acid in which a hydrogen atom of the amino group may be substituted with a substituent, polyoxyethylene alkyl ether phosphoric acid, polyoxyethylene polycyclic phenyl ether phosphoric acid, alkyl phosphoric acid, and salts thereof; and a second reagent which comprises an enzyme that catalyzes a reaction of oxidizing glycated hemoglobin to generate hydrogen peroxide.

[12] A kit for measuring glycated hemoglobin in a hemoglobin-containing sample, comprising:

a first reagent which comprises an enzyme that catalyzes a reaction of oxidizing glycated hemoglobin to generate hydrogen peroxide; and a second reagent which comprises at least one anionic surfactant selected from the group consisting of N-acyl taurine in which a hydrogen atom of the amino group may be substituted with a substituent, alkyl sulfoacetic acid, polyoxyethylene alkyl ether acetic acid, N-acyl amino acid in which a hydrogen atom of the amino group may be substituted with a substituent, polyoxyethylene alkyl ether phosphoric acid, polyoxyethylene polycyclic phenyl ether phosphoric acid, alkyl phosphoric acid, and salts thereof.

[13] The kit according to [11] or [12],
wherein a peroxidase and a leuco-type chromogen are further contained in the first reagent and the second reagent, respectively, or in the second reagent and the first reagent, respectively.

[14] The kit according to [13],
wherein the leuco-type chromogen is a phenothiazine-based chromogen.

[15] The kit according to [14],
wherein the phenothiazine-based chromogen is 10-(carboxymethylaminocarbonyl)-3,7-bis(dimethylamino)phenothiazine or a salt thereof.

Effects of the Invention

According to the present invention, a method, a reagent and a kit are provided for measuring glycated hemoglobin in a hemoglobin-containing sample in a simple and highly sensitive manner.

BRIEF DESCRIPTION OF DRAWINGS

FIG. 1 is a graph showing a relationship between an HbA1c concentration and an absorbance difference ΔE in measurement of HbA1c in a hemoglobin-containing sample using a kit A comprising FPDX-47Δ3 in a second reagent. The vertical axis represents the absorbance difference ΔE (Abs×10,000), and the horizontal axis represents the HbA1c concentration (μmol/L).

MODE FOR CARRYING OUT THE INVENTION (1) Method for Measuring Glycated Hemoglobin in Hemoglobin-Containing Sample The method for measuring glycated hemoglobin in a hemoglobin-containing sample of the present invention is a method characterized by reacting glycated hemoglobin in the hemoglobin-containing sample with an enzyme that catalyzes a reaction of oxidizing the glycated hemoglobin to generate hydrogen peroxide, in the presence of at least one anionic surfactant selected from the group consisting of N-acyl taurine in which a hydrogen atom of the amino group may be substituted with a substituent, alkyl sulfoacetic acid, polyoxyethylene alkyl ether acetic acid, N-acyl amino acid in which a hydrogen atom of the amino group may be substituted with a substituent, polyoxyethylene alkyl ether phosphoric acid, polyoxyethylene polycyclic phenyl ether phosphoric acid, alkyl phosphoric acid, and salts thereof, to generate hydrogen peroxide, and measuring the generated hydrogen peroxide.

Specifically, the method is a measuring method comprising the following steps.

(i) A step of reacting glycated hemoglobin in the hemoglobin-containing sample with an enzyme that catalyzes a reaction of oxidizing the glycated hemoglobin to generate hydrogen peroxide, in an aqueous medium comprising at least one anionic surfactant selected from the group consisting of N-acyl taurine in which a hydrogen atom of the amino group may be substituted with a substituent, alkyl sulfoacetic acid, polyoxyethylene alkyl ether acetic acid, N-acyl amino acid in which a hydrogen atom of the amino group may be substituted with a substituent, polyoxyethylene alkyl ether phosphoric acid, polyoxyethylene polycyclic phenyl ether phosphoric acid, alkyl phosphoric acid, and salts thereof, to generate hydrogen peroxide;

(ii) a step of measuring the hydrogen peroxide generated in step (i); and (iii) a step of determining the concentration of the glycated hemoglobin in the hemoglobin-containing sample by correlating an amount of the hydrogen peroxide measured in step (ii) with a calibration curve showing a relationship between an amount of hydrogen peroxide and the concentration of glycated hemoglobin, prepared in advance by performing measurement according to above (i) and (ii) using glycated hemoglobin with known concentrations.

In addition, the method for measuring glycated hemoglobin in a hemoglobin-containing sample of the present invention also includes a method of calculating a proportion of an amount of the glycated hemoglobin to a total amount of hemoglobin (that is, a combined total amount of hemoglobin and glycated hemoglobin) in the hemoglobin-containing sample. In this case, the method for measuring glycated hemoglobin in a hemoglobin-containing sample of the present invention is specifically a measuring method comprising the following steps.

(i) A step of measuring a total amount of hemoglobin in the hemoglobin-containing sample;

(ii) a step of reacting glycated hemoglobin in the hemoglobin-containing sample with an enzyme that catalyzes a reaction of oxidizing the glycated hemoglobin to generate hydrogen peroxide, in an aqueous medium containing at least one anionic surfactant selected from the group consisting of N-acyl taurine in which a hydrogen atom of the amino group may be substituted with a substituent, alkyl sulfoacetic acid, polyoxyethylene alkyl ether acetic acid, N-acyl amino acid in which a hydrogen atom of the amino group may be substituted with a substituent, polyoxyethylene alkyl ether phosphoric acid, polyoxyethylene polycyclic phenyl ether phosphoric acid, alkyl phosphoric acid, and salts thereof, to generate hydrogen peroxide;

(iii) a step of measuring the hydrogen peroxide generated in step (ii);

(iv) a step of measuring an amount of the glycated hemoglobin in the hemoglobin-containing sample by correlating an amount of the hydrogen peroxide measured in step (iii) with a calibration curve showing a relationship between an amount of hydrogen peroxide and the concentration of glycated hemoglobin, prepared in advance by performing measurement according to the above (ii) and (iii) using glycated hemoglobin with known concentrations; and (v) calculating a proportion of an amount of the glycated hemoglobin to a total amount of hemoglobin in the hemoglobin-containing sample, based on the total amount of hemoglobin measured in step (i) and the amount of glycated hemoglobin amount measured in step (iv).

The measurement of the total amount of hemoglobin in step (i) can also be performed after adding, to the hemoglobin-containing sample, at least one anionic surfactant selected from the group consisting of N-acyl taurine in which a hydrogen atom of the amino group may be substituted with a substituent, alkyl sulfoacetic acid, polyoxyethylene alkyl ether acetic acid, N-acyl amino acid in which a hydrogen atom of the amino group may be substituted with a substituent, polyoxyethylene alkyl ether phosphoric acid, polyoxyethylene polycyclic phenyl ether phosphoric acid, alkyl phosphoric acid, and salts thereof, to denature hemoglobin and glycated hemoglobin in the hemoglobin-containing sample.

The hemoglobin-containing sample in the measuring method of the present invention is not particularly limited as long as the hemoglobin-containing sample is a sample which contains hemoglobin and to which the method for measuring glycated hemoglobin of the present invention can be applied. Examples thereof include whole blood, blood cells, a sample in which plasma is mixed in blood cells, and samples obtained by subjecting these samples to hemolysis treatment. The hemolysis treatment is not particularly limited as long as the hemolysis treatment is a treatment for hemolyzing whole blood, blood cells, or a sample in which plasma is mixed in blood cells. Examples thereof include a physical method, a chemical method, and a biological method. Examples of the physical method include a method using a hypotonic solution such as distilled water and a method using ultrasonic waves. Examples of the chemical method include a method using an organic solvent such as methanol, ethanol, and acetone, and a method using a polyoxyethylene-based surfactant. Examples of the biological method include a method using an antibody or complement.

Glycated hemoglobin in the present invention is formed by binding of saccharides such as glucose to hemoglobin, and includes hemoglobin A1a, hemoglobin A1b, HbA1c, and the like, with HbA1c being preferred.

In the present invention, at least one anionic surfactant selected from the group consisting of N-acyl taurine in which a hydrogen atom of the amino group may be substituted with a substituent, alkyl sulfoacetic acid, polyoxyethylene alkyl ether acetic acid, N-acyl amino acid in which a hydrogen atom of the amino group may be substituted with a substituent, polyoxyethylene alkyl ether phosphoric acid, polyoxyethylene polycyclic phenyl ether phosphoric acid, alkyl phosphoric acid, and salts thereof is used.

In the present invention, in the N-acyl taurine in which a hydrogen atom of the amino group may be substituted with a substituent, examples of the substituent include an alkyl group, a halogenated alkyl group, and a phenyl group. Examples of the halogenated alkyl group include a fluoroalkyl group, a chloroalkyl group, a bromoalkyl group, and an iodoalkyl group. In the alkyl group and the halogenated alkyl group, examples of the alkyl include an alkyl having 1 to 6 carbon atoms. Examples of the alkyl having 1 to 6 carbon atoms include methyl, ethyl, propyl, butyl, pentyl, and hexyl. In the present invention, examples of the N-acyl taurine in which a hydrogen atom of the amino group may be substituted with a substituent include N-acyl taurine and N-acyl-N-alkyl taurine, with N-acyl-N-alkyl taurine being preferred.

In the N-acyl taurine in which a hydrogen atom of the amino group may be substituted with a substituent, examples of the acyl include an acyl having 8 to 20 carbon atoms, with an acyl having 10 to 18 carbon atoms being preferred. Examples of the acyl having 8 to 20 carbon atoms include octanoyl, nonanoyl, decanoyl, undecanoyl, dodecanoyl (lauroyl), tridecanoyl, tetradecanoyl, pentadecanoyl, hexadecanoyl (palmitoyl), heptadecanoyl, octadecanoyl (stearoyl), oleoyl, vaccenoyl, linoleoyl, nonadecanoyl, and eicosanoyl. Examples of the acyl having 10 to 18 carbon atoms include decanoyl, undecanoyl, dodecanoyl (lauroyl), tridecanoyl, tetradecanoyl, pentadecanoyl, hexadecanoyl (palmitoyl), heptadecanoyl, octadecanoyl (stearoyl), oleoyl, vaccenoyl, and linoleoyl.

In the N-acyl-N-alkyl taurine, examples of the alkyl include an alkyl having 1 to 6 carbon atoms. Examples of the alkyl having 1 to 6 carbon atoms include methyl, ethyl, propyl, butyl, pentyl, and hexyl.

In addition, in the present invention, the N-acyl taurine in which a hydrogen atom of the amino group may be substituted with a substituent may be a salt. Examples of the salt include a sodium salt, a potassium salt, an ammonium salt, a magnesium salt, a calcium salt, and a monoethanolamine salt.

As specific examples (product) of the N-acyl taurine in which a hydrogen atom of the amino group may be substituted with a substituent, or a salt thereof, for example, NIKKOL LMT (sodium N-lauroyl-N-methyl taurine; manufactured by Nikko Chemicals Co., Ltd.), NIKKOL PMT (sodium N-palmitoyl-N-methyltaurine; manufactured by Nikko Chemicals Co., Ltd.), NIKKOL MMT (sodium N-myristoyl-N-methyltaurine; manufactured by Nikko Chemicals Co., Ltd.), NIKKOL SMT (sodium N-stearoyl-N-methyltaurine; manufactured by Nikko Chemicals Co., Ltd.), and the like can be mentioned.

In the method for measuring glycated hemoglobin of the present invention, the concentration of the N-acyl taurine in which a hydrogen atom of the amino group may be substituted with a substituent, or a salt thereof in a reaction solution is usually 0.001% to 10%, and preferably 0.01% to 5%.

In the present invention, in the alkyl sulfoacetic acid, examples of the alkyl include an alkyl having 8 to 20 carbon atoms, with an alkyl having 10 to 18 carbon atoms being preferred. Examples of the alkyl having 8 to 20 carbon atoms include octyl, nonyl, decyl, undecyl, dodecyl (lauryl), tridecyl, tetradecyl (myristyl), pentadecyl, hexadecyl (cetyl), heptadecyl, octadecyl (stearyl), oleyl, nonadecyl, and icosyl. Examples of the alkyl having 10 to 18 carbon atoms include decyl, undecyl, dodecyl (lauryl), tridecyl, tetradecyl (myristyl), pentadecyl, hexadecyl (cetyl), heptadecyl, octadecyl (stearyl), and oleyl.

In addition, in the present invention, the alkyl sulfoacetic acid may be a salt. Examples of the salt include a sodium salt, a potassium salt, an ammonium salt, a magnesium salt, a calcium salt, and a monoethanolamine salt.

As specific examples (product) of the alkyl sulfoacetic acid or a salt thereof, for example, NIKKOL LSA-F (sodium lauryl sulfoacetate; manufactured by Nikko Chemicals Co., Ltd.) and the like can be mentioned.

In the method for measuring glycated hemoglobin of the present invention, the concentration of the alkyl sulfoacetic acid or a salt thereof in a reaction solution is usually 0.001 to 10%, and preferably 0.01 to 5%.

In the present invention, in the polyoxyethylene alkyl ether acetic acid, examples of the alkyl include an alkyl having 8 to 20 carbon atoms, with an alkyl having 10 to 18 carbon atoms being preferred. Examples of the alkyl having 8 to 20 carbon atoms include octyl, nonyl, decyl, undecyl, dodecyl (lauryl), tridecyl, tetradecyl (myristyl), pentadecyl, hexadecyl (cetyl), heptadecyl, octadecyl (stearyl), oleyl, nonadecyl, and icosyl. Examples of the alkyl having 10 to 18 carbon atoms include decyl, undecyl, dodecyl (lauryl), tridecyl, tetradecyl (myristyl), pentadecyl, hexadecyl (cetyl), heptadecyl, octadecyl (stearyl), and oleyl.

In addition, in the present invention, the polyoxyethylene alkyl ether acetic acid may be a salt. In the polyoxyethylene alkyl ether acetic acid salt, examples of the salt include a sodium salt, a potassium salt, an ammonium salt, a magnesium salt, a calcium salt, and a monoethanolamine salt.

As specific examples (product) of the polyoxyethylene alkyl ether acetic acid or a salt thereof, for example, NIKKOL AKYPO RLM 45 NV (sodium polyoxyethylene lauryl ether acetate; manufactured by Nikko Chemicals Co., Ltd.), NIKKOL AKYPO RLM 45 (polyoxyethylene lauryl ether acetate; manufactured by Nikko Chemicals Co., Ltd.), NIKKOL AKYPO RLM 100 (polyoxyethylene lauryl ether acetate; manufactured by Nikko Chemicals Co., Ltd.), NIKKOL ECT-3NEX (sodium polyoxyethylene tridecyl ether acetate; manufactured by Nikko Chemicals Co., Ltd.), NIKKOL ECTD-3NEX (sodium polyoxyethylene tridecyl ether acetate; manufactured by Nikko Chemicals Co., Ltd.), NIKKOL ECTD-6NEX (sodium polyoxyethylene tridecyl ether acetate; manufactured by Nikko Chemicals Co., Ltd.), NEOHITENOL ECL-45 (sodium polyoxyethylene lauryl ether acetate; manufactured by DKS Co., Ltd.), and the like can be mentioned.

In the method for measuring glycated hemoglobin of the present invention, the concentration of polyoxyethylene alkyl ether acetic acid or a salt thereof in a reaction solution is usually 0.001% to 10%, and preferably 0.01% to 5%.

In the present invention, in the N-acyl amino acid in which a hydrogen atom of the amino group may be substituted with a substituent, examples of the substituent include an alkyl group, a halogenated alkyl group, and a phenyl group. Examples of the halogenated alkyl group include a fluoroalkyl group, a chloroalkyl group, a bromoalkyl group, and an iodoalkyl group. In the alkyl group and the halogenated alkyl group, examples of the alkyl include an alkyl having 1 to 6 carbon atoms. Examples of the alkyl having 1 to 6 carbon atoms include methyl, ethyl, propyl, butyl, pentyl, and hexyl.

In the present invention, examples of the N-acyl amino acid in which a hydrogen atom of the amino group may be substituted with a substituent include N-acyl amino acid and N-acyl-N-alkyl amino acid, with N-acyl-N-alkyl amino acid being preferred.

In the N-acyl amino acid in which a hydrogen atom of the amino group may be substituted with a substituent, examples of the amino acid include glycine, sarcosine, alanine, β-alanine, valine, leucine, isoleucine, lysine, arginine, serine, threonine, cysteine, methionine, aspartic acid, asparagine, glutamic acid, glutamine, phenylalanine, tyrosine, tryptophan, histidine, and proline.

In the N-acyl amino acid in which a hydrogen atom of the amino group may be substituted with a substituent, examples of the acyl include an acyl having 8 to 20 carbon atoms, with an acyl having 10 to 18 carbon atoms being preferred. Examples of the acyl having 8 to 20 carbon atoms include octanoyl, nonanoyl, decanoyl, undecanoyl, dodecanoyl (lauroyl), tridecanoyl, tetradecanoyl, pentadecanoyl, hexadecanoyl (palmitoyl), heptadecanoyl, octadecanoyl (stearoyl), oleoyl, vaccenoyl, linoleoyl, nonadecanoyl, and eicosanoyl. Examples of the acyl having 10 to 18 carbon atoms include decanoyl, undecanoyl, dodecanoyl (lauroyl), tridecanoyl, tetradecanoyl, pentadecanoyl, hexadecanoyl (palmitoyl), heptadecanoyl, octadecanoyl (stearoyl), oleoyl, vaccenoyl, and linoleoyl.

In the N-acyl-N-alkyl amino acid, examples of the alkyl include an alkyl having 1 to 6 carbon atoms. Examples of the alkyl having 1 to 6 carbon atoms include methyl, ethyl, propyl, butyl, pentyl, and hexyl.

In addition, in the present invention, the N-acyl amino acid in which a hydrogen atom of the amino group may be substituted with a substituent may be a salt. Examples of the salt include a sodium salt, a potassium salt, an ammonium salt, a magnesium salt, a calcium salt, and a monoethanolamine salt.

As specific examples (products) of the N-acyl amino acid in which a hydrogen atom of the amino group may be substituted with a substituent, or a salt thereof, for example, NIKKOL ALANINATE LN-30 (sodium N-lauroyl-N-methyl-β-alanine; manufactured by Nikko Chemicals Co., Ltd.), NIKKOL SARCOSINATE PN (sodium N-palmitoyl sarcosine; manufactured by Nikko Chemicals Co., Ltd.), NIKKOL SARCOSINATE LN (sodium N-lauroyl sarcosine; manufactured by Nikko Chemicals Co., Ltd.), NIKKOL SARCOSINATE MN (sodium N-myristoyl sarcosine; manufactured by Nikko Chemicals Co., Ltd.), NIKKOL SARCOSINATE OH (N-oleoyl sarcosine; manufactured by Nikko Chemicals Co., Ltd.), and the like can be mentioned.

In the method for measuring glycated hemoglobin of the present invention, the concentration of the N-acyl amino acid in which a hydrogen atom of the amino group may be substituted with a substituent, or a salt thereof in a reaction solution is usually 0.001% to 10%, and preferably 0.01% to 5%.

In the polyoxyethylene alkyl ether phosphoric acid in the present invention, examples of the alkyl include an alkyl having 8 to 20 carbon atoms, with an alkyl having 10 to 18 carbon atoms being preferred. Examples of the alkyl having 8 to 20 carbon atoms include octyl, nonyl, decyl, undecyl, dodecyl (lauryl), tridecyl, tetradecyl (myristyl), pentadecyl, hexadecyl (cetyl), heptadecyl, octadecyl (stearyl), oleyl, nonadecyl, and icosyl. Examples of the alkyl having 10 to 18 carbon atoms include decyl, undecyl, dodecyl (lauryl), tridecyl, tetradecyl (myristyl), pentadecyl, hexadecyl (cetyl), heptadecyl, octadecyl (stearyl), and oleyl.

In addition, in the present invention, the polyoxyethylene alkyl ether phosphoric acid may be a salt. Examples of the salt include a sodium salt, a potassium salt, an ammonium salt, a magnesium salt, a calcium salt, and a monoethanolamine salt.

As specific examples (product) of the polyoxyethylene alkyl ether phosphoric acid or a salt thereof, for example, PLYSURF A212C (polyoxyethylene tridecyl ether phosphoric acid; manufactured by DKS Co., Ltd.), PLYSURF A215C (polyoxyethylene tridecyl ether phosphoric acid; manufactured by DKS Co., Ltd.), PLYSURF A208B (polyoxyethylene lauryl ether phosphoric acid; manufactured by DKS Co., Ltd.), PLYSURF A219B (polyoxyethylene lauryl ether phosphoric acid; manufactured byDKS Co., Ltd.), and the like can be mentioned.

In the method for measuring glycated hemoglobin of the present invention, the concentration of the polyoxyethylene alkyl ether phosphoric acid or a salt thereof in a reaction solution is usually 0.001% to 10%, and preferably 0.01% to 5%.

In the polyoxyethylene polycyclic phenyl ether phosphoric acid in the present invention, as the polycyclic phenyl, a phenyl group substituted with two or more groups (substituents) having one aromatic ring in the group, a phenyl group substituted with one or plural groups (substituents) having two or more aromatic rings in the group, and the like can be mentioned.

In addition, in the present invention, the polyoxyethylene polycyclic phenyl ether phosphoric acid may be a salt. Examples of the salt include a sodium salt, a potassium salt, an ammonium salt, a magnesium salt, a calcium salt, and a monoethanolamine salt.

As specific examples (product) of the polyoxyethylene polycyclic phenyl ether phosphoric acid or a salt thereof, for example, PLYSURF AL (polyoxyethylene styrenated phenyl ether phosphoric acid; manufactured by DKS Co., Ltd.), PLYSURF AL12H (polyoxyethylene styrenated phenyl ether phosphoric acid; manufactured by DKS Co., Ltd.), and the like can be mentioned.

In the method for measuring glycated hemoglobin of the present invention, the concentration of the polyoxyethylene polycyclic phenyl ether phosphoric acid or a salt thereof in a reaction solution is usually 0.001% to 10%, and preferably 0.01% to 5%.

In the alkyl phosphoric acid in the present invention, examples of the alkyl include an alkyl having 8 to 20 carbon atoms, with an alkyl having 10 to 18 carbon atoms being preferred. Examples of the alkyl having 8 to 20 carbon atoms include octyl, nonyl, decyl, undecyl, dodecyl (lauryl), tridecyl, tetradecyl (myristyl), pentadecyl, hexadecyl (cetyl), heptadecyl, octadecyl (stearyl), oleyl, nonadecyl, and icosyl. Examples of the alkyl having 10 to 18 carbon atoms include decyl, undecyl, dodecyl (lauryl), tridecyl, tetradecyl (myristyl), pentadecyl, hexadecyl (cetyl), heptadecyl, octadecyl (stearyl), and oleyl.

In addition, in the present invention, the alkyl phosphoric acid may be a salt. Examples of the salt include a sodium salt, a potassium salt, an ammonium salt, a magnesium salt, a calcium salt, and a monoethanolamine salt.

As specific examples (product) of the alkyl phosphoric acid or a salt thereof, for example, NIKKOL SLP-N (sodium lauryl phosphate; manufactured by Nikko Chemicals Co., Ltd.), NIKKOL HOSTEN HLP (lauryl phosphoric acid; manufactured by Nikko Chemicals Co., Ltd.), and the like can be mentioned.

In the method for measuring glycated hemoglobin of the present invention, the concentration of the alkyl phosphoric acid or a salt thereof in a reaction solution is usually 0.001% to 10%, and preferably 0.01% to 5%.

A total amount of hemoglobin can be measured by a known method, for example, a cyanmethemoglobin method, an oxyhemoglobin method, or an SLS-hemoglobin method. The total amount of hemoglobin can be measured by applying the cyanmethemoglobin method, the oxyhemoglobin method, the SLS-hemoglobin method, or the like not only to a hemoglobin-containing sample itself but also to a sample obtained by addition of at least one anionic surfactant selected from the group consisting of N-acyl taurine in which a hydrogen atom of the amino group may be substituted with a substituent, alkyl sulfoacetic acid, polyoxyethylene alkyl ether acetic acid, N-acyl amino acid in which a hydrogen atom of the amino group may be substituted with a substituent, polyoxyethylene alkyl ether phosphoric acid, polyoxyethylene polycyclic phenyl ether phosphoric acid, alkyl phosphoric acid, and salts thereof to a hemoglobin-containing sample.

A reaction between glycated hemoglobin in a hemoglobin-containing sample with an enzyme that catalyzes a reaction of oxidizing the glycated hemoglobin to generate hydrogen peroxide, in an aqueous medium comprising at least one anionic surfactant selected from the group consisting of N-acyl taurine in which a hydrogen atom of the amino group may be substituted with a substituent, alkyl sulfoacetic acid, polyoxyethylene alkyl ether acetic acid, N-acyl amino acid in which a hydrogen atom of the amino group may be substituted with a substituent, polyoxyethylene alkyl ether phosphoric acid, polyoxyethylene polycyclic phenyl ether phosphoric acid, alkyl phosphoric acid, and salts thereof, can be carried out under any condition as long as the condition enables action of the enzyme that catalyzes a reaction of oxidizing the glycated hemoglobin to generate hydrogen peroxide on the glycated hemoglobin.

The reaction between the glycated hemoglobin in the hemoglobin-containing sample with the enzyme that catalyzes a reaction of oxidizing the glycated hemoglobin to generate hydrogen peroxide is preferably carried out in an aqueous medium.

The aqueous medium is not particularly limited as long as the aqueous medium enables the method for measuring glycated hemoglobin of the present invention, and examples thereof include deionized water, distilled water, and a buffer solution, with a buffer solution being preferred.

A pH of the aqueous medium is not particularly limited as long as the pH enables the method for measuring glycated hemoglobin of the present invention, and is, for example, pH 4 to 10. In a case where the buffer solution is used as the aqueous medium, it is desirable to use a buffer according to a pH to be set. Examples of the buffer used for the buffer solution include a tris(hydroxymethyl)aminomethane buffer, a phosphate buffer, a borate buffer, and a Good's buffer.

Examples of the Good's buffer include 2-morpholinoethane sulfonic acid (MES), bis(2-hydroxyethyl)iminotris(hydroxymethyl)methane (Bis-Tris), N-(2-acetamido)iminodiacetic acid (ADA), piperazine-N,N'-bis(2-ethane sulfonic acid) (PIPES), N-(2-acetamido)-2-aminoethane sulfonic acid (ACES), 3-morpholino-2-hydroxypropane sulfonic acid (MOPSO), N,N-bis(2-hydroxyethyl)-2-aminoethane sulfonic acid (BES), 3-morpholinopropane sulfonic acid (MOPS), N-[tris(hydroxymethyl)methyl]-2-aminoethane sulfonic acid (TES), 2-[4-(2-hydroxyethyl)-1-piperazinyl] ethane sulfonic acid (HEPES), 3-[N,N-bis(2-hydroxyethyl) amino]-2-hydroxypropane sulfonic acid (DIPSO), N-[tris (hydroxymethyl)methyl]-2-hydroxy-3-aminopropane sulfonic acid (TAPSO), piperazine-N,N'-bis(2-hydroxypropanesulfonic acid) (POPSO), 3-[4-(2-hydroxyethyl)-1-piperazinyl]-2-hydroxypropane sulfonic acid (HEPPSO), 3-[4-(2-hydroxyethyl)-1-piperazinyl]propane sulfonic acid [(H) EPPS], N-[tris(hydroxymethyl)methyl]glycine (Tricine), N,N-bis(2-hydroxyethyl)glycine (Bicine), N-tris(hydroxymethyl)methyl-3-aminopropane sulfonic acid (TAPS), N-cyclohexyl-2-aminoethane sulfonic acid (CHES), N-cyclohexyl-3-amino-2-hydroxypropane sulfonic acid (CAPSO), and N-cyclohexyl-3-aminopropane sulfonic acid (CAPS).

The concentration of the buffer solution is usually 0.001 to 2.0 mol/L, and preferably 0.005 to 1.0 mol/L.

In the reaction between the glycated hemoglobin in the hemoglobin-containing sample with the enzyme that catalyzes a reaction of oxidizing the glycated hemoglobin to generate hydrogen peroxide, a reaction temperature is not particularly limited as long as the reaction temperature enables the method for measuring glycated hemoglobin of the present invention, and is usually 10° C. to 50° C., and preferably 20° C. to 40° C. In addition, a reaction time in the reaction is not particularly limited as long as the reaction time enables the method for measuring glycated hemoglobin of the present invention, and is usually 1 minute to 3 hours, and preferably 2.5 minutes to 1 hour. The concentration of the enzyme that catalyzes a reaction of oxidizing glycated hemoglobin to generate hydrogen peroxide is not particularly limited as long as the concentration enables the method for measuring glycated hemoglobin of the present invention, and is usually 0.1 to 30 kU/L, and preferably 0.2 to 15 kU/L.

In the present invention, an enzyme activity (U) of the enzyme that catalyzes a reaction of oxidizing glycated hemoglobin to generate hydrogen peroxide was calculated by the following method.

<Reagent for Measuring Enzyme Activity>
First Reagent
Phosphate buffer solution (pH 8.0) 0.1 mmol/L
N-Ethyl-N-(3-methylphenyl)-N'-succinyl ethylenediamine (EMSE) 0.3 g/L
Peroxidase 3 kU/L
4-Aminoantipyrine 0.1 g/L
Second Reagent
Fructosyl valine aqueous solution 1.7 mmol/L
The fructosyl valine aqueous solution was prepared by the method described in J. Agric. Food Chem., Vol. 24, No. 1, pp. 70 to 73 (1976).
<Sample Diluent>
Phosphate buffer solution (pH 8.0) 10 mmol/L
Bovine serum albumin 0.15%
<Sample>
FPDX-47Δ3 (an enzyme that catalyzes a reaction of oxidizing glycated hemoglobin to generate hydrogen peroxide) diluted with the above-mentioned sample diluent
<Measurement>

The sample (2 μL) and the first reagent (150 μL) of the reagent for measuring an enzyme activity were added to a reaction cuvetteto react at 37° C. for 3 minutes (first reaction). Then, the second reagent (20 μL) of the reagent for measuring an enzyme activity were added, and an absorbance [$Abs_{enzyme\ (after}$ 3 minutes)] of a reaction solution 3 minutes after addition of the second reagent and an absorbance [$Abs_{enzyme\ (after}$ 5 minutes)] of a reaction solution 5 minutes after addition of the second reagent were both measured at a main wavelength of 546 nm and a sub-wavelength of 700 nm. The $Abs_{enzyme\ (after}$ 3 minutes) was subtracted from the $Abs_{enzyme\ (after}$ 5 minutes) to calculate an absorbance difference $\Delta Abs'_{enzyme}$, and the calculated absorbance difference $\Delta Abs'_{enzyme}$ was divided by 2 (minutes) to calculate an absorbance change amount per minute $\Delta Abs'_{enzyme}$/min.

An absorbance difference $\Delta Abs'_{blank}$/min was calculated by the same method as the above method except that the sample diluent was used in place of the above sample.

An absorbance difference $\Delta Abs_{enzyme}$/min for the enzyme was determined by subtracting the $\Delta Abs'_{blank}$/min from the calculated $\Delta Abs'_{enzyme}$/min.

<Enzyme Activity>

Based on the $\Delta Abs_{enzyme}$/min determined above, an enzyme activity was calculated by the following expression (I).

$$\text{Enzymatic activity } (kU/L) = \frac{\Delta Abs_{enzyme}/\min \times 0.172 \text{ (mL)} \times \text{dilution rate}}{33.8 \times 0.5 \times 0.002 \text{ (mL)}} \quad (I)$$

In expression (I), 33.8 is an extinction coefficient in mmol [$(mmol/L)^{-1} \cdot cm^{-1}$] of a quinoneimine dye generated by reaction.

In expression (I), 0.5 is the number of mol of a quinoneimine dye generated by 1 mol of hydrogen peroxide.

The enzyme that catalyzes a reaction of oxidizing glycated hemoglobin to generate hydrogen peroxide is not particularly limited as long as the enzyme can act on glycated hemoglobin in a hemoglobin-containing sample to generate hydrogen peroxide from the glycated hemoglobin, and examples thereof include the enzymes described in PCT International Publication No. WO2015/005258, and the amadoriases described in PCT International Publication No. WO2015/060429. Specifically, FPDX-18A, FPDX-18B, FPDX-18C, FPDX-18D, FPDX 19 to 46, and the like described in PCT International Publication No. WO2015/005258 can be mentioned. As specific examples of modified products of the enzymes, for example, FPDX-47Δ3 and the like produced in Reference Example 1 as described later can be mentioned.

The method for measuring the generated hydrogen peroxide is not particularly limited as long as the method enables measuring hydrogen peroxide. Examples thereof include a method using an electrode, a method using a reagent for measuring hydrogen peroxide, and the like, with a method using a reagent for measuring hydrogen peroxide being preferred. The reagent for measuring hydrogen peroxide is a reagent for converting hydrogen peroxide into a detectable substance. Examples of the detectable substance include a dye, light (luminescence), and fluorescence, with a dye being preferred.

In a case where the detectable substance is a dye, as the reagent for measuring hydrogen peroxide, a reagent containing a peroxidative substance such as a peroxidase and an oxidative coloring-type chromogen and the like can be mentioned. As the oxidative coloring-type chromogen, an oxidative coupling-type chromogen and a leuco-type chromogen and the like can be mentioned, with a leuco-type chromogen being preferred.

In the present invention, the leuco-type chromogen is a substance which is converted into a dye by itself in the presence of hydrogen peroxide and a peroxidative substance. Examples of the peroxidative substance include a peroxidase.

Examples of the leuco-type chromogen include a phenothiazine-based chromogen, a triphenylmethane-based chromogen, a diphenylamine-based chromogen, o-phenylenediamine, hydroxypropionic acid, diaminobenzidine, and tetramethylbenzidine, with a phenothiazine-based chromogen being preferred.

Examples of the phenothiazine-based chromogen include 10-N-carboxymethylcarbamoyl-3,7-bis(dimethylamino)-10H-phenothiazine (CCAP), 10-N-methylcarbamoyl-3,7-bis(dimethylamino)-10H-phenothiazine (MCDP), and 10-N-(carboxymethylaminocarbonyl)-3,7-bis(dimethylamino)-10H-phenothiazine sodium salt (DA-67). Among the phenothiazine-based chromogens, 10-N-(carboxymethylaminocarbonyl)-3,7-bis(dimethylamino)-10H-phenothiazine sodium salt (DA-67) is particularly preferable.

Examples of the triphenylmethane-based chromogen include N,N,N',N',N",N"-hexa(3-sulfopropyl)-4,4',4"-triaminotriphenyl methane (TPM-PS). Examples of the diphenylamine-based chromogen include N-(carboxymethylaminocarbonyl)-4,4'-bis(dimethylamino)diphenylamine sodium salt (DA-64), 4,4'-bis(dimethylamino)diphenylamine, and bis[3-bis(4-chlorophenyl)methyl-4-dimethylaminophenyl]amine (BCMA).

In the present invention, the oxidative coupling-type chromogen is a substance that forms a dye by oxidative-coupling of two compounds in the presence of hydrogen peroxide and a peroxidative substance. As a combination of the two compounds, a combination of a coupler and an aniline, a combination of a coupler and a phenol, and the like can be mentioned.

Examples of the coupler include 4-aminoantipyrine (4-AA) and 3-methyl-2-benzothiazolinone hydrazine.

Examples of the anilines include N-(3-sulfopropyl)aniline, N-ethyl-N-(2-hydroxy-3-sulfopropyl)-3-methylaniline (TOOS), N-ethyl-N-(2-hydroxy-3-sulfopropyl)-3,5-dimethylaniline (MAOS), N-ethyl-N-(2-hydroxy-3-sulfopropyl)-3,5-dimethoxyaniline (DAOS), N-ethyl-N-(3-sulfopropyl)-3-methylaniline (TOPS), N-(2-hydroxy-3-sulfopropyl)-3,5-dimethoxyaniline (HDAOS), N,N-dimethyl-3-methylaniline, N,N-bis(3-sulfopropyl)-3,5-dimethoxyaniline, N-ethyl-N-(3-sulfopropyl)-3-methoxyaniline, N-ethyl-N-(3-sulfopropyl)aniline, N-ethyl-N-(3-sulfopropyl)-3,5-dimethoxaniline, N-(3-sulfopropyl)-3,5-dimethoxyaniline, N-ethyl-N-(3-sulfopropyl)-3,5-dimethylaniline, N-ethyl-N-(2-hydroxy-3-sulfopropyl)-3-methoxyaniline, N-ethyl-N-(2-hydroxy-3-sulfopropyl)aniline, N-ethyl-N-(3-methylphenyl)-N'-succinyl ethylenediamine (EMSE), N-ethyl-N-(3-methylphenyl)-N'-acetyl ethylenediamine, and N-ethyl-N-(2-hydroxy-3-sulfopropyl)-4-fluoro-3,5-dimethoxyaniline (F-DAOS).

Examples of the phenols include phenol, 4-chlorophenol, and 3-methylphenol, 3-hydroxy-2,4,6-triiodobenzoic acid (HTIB).

In a case where the detectable substance is light (luminescence), as the reagent for measuring hydrogen peroxide, a reagent comprising a peroxidative substance such as a peroxidase and a chemiluminescent substance and the like can be mentioned. Examples of the chemiluminescent substance include luminol, isoluminol, lucigenin, and acridinium ester.

In a case where the detectable substance is fluorescence, as the reagent for measuring hydrogen peroxide, a reagent comprising a peroxidative substance such as a peroxidase and a fluorescent substance and the like can be mentioned. Examples of the fluorescent substance include 4-hydroxyphenylacetic acid, 3-(4-hydroxyphenyl)propionic acid, and coumarin.

(2) Reagent for Measuring Glycated Hemoglobin in Hemoglobin-Containing Sample

The reagent for measuring glycated hemoglobin in a hemoglobin-containing sample of the present invention is a reagent comprising an enzyme that catalyzes a reaction of oxidizing the glycated hemoglobin to generate hydrogen peroxide, and at least one anionic surfactant selected from the group consisting of N-acyl taurine in which a hydrogen atom of the amino group may be substituted with a substituent, alkyl sulfoacetic acid, polyoxyethylene alkyl ether acetic acid, N-acyl amino acid in which a hydrogen atom of the amino group may be substituted with a substituent, polyoxyethylene alkyl ether phosphoric acid, polyoxyethylene polycyclic phenyl ether phosphoric acid, alkyl phosphoric acid, and salts thereof, and is used in the method for measuring glycated hemoglobin in a hemoglobin-containing sample of the present invention. The measuring reagent of the present invention may further comprise a reagent for measuring hydrogen peroxide.

In the measuring reagent of the present invention, examples of the enzyme that catalyzes a reaction of oxidizing glycated hemoglobin to generate hydrogen peroxide; the at least one anionic surfactant selected from the group consisting of N-acyl taurine in which a hydrogen atom of the amino group may be substituted with a substituent, alkyl sulfoacetic acid, polyoxyethylene alkyl ether acetic acid, N-acyl amino acid in which a hydrogen atom of the amino group may be substituted with a substituent, polyoxyethylene alkyl ether phosphoric acid, polyoxyethylene polycyclic phenyl ether phosphoric acid, alkyl phosphoric acid, and salts thereof; and the reagent for measuring hydrogen peroxide comprises the enzyme that catalyzes a reaction of oxidizing glycated hemoglobin to generate hydrogen peroxide; the at least one anionic surfactant selected from the group consisting of N-acyl taurine in which a hydrogen atom of the amino group may be substituted with a substituent, alkyl sulfoacetic acid, polyoxyethylene alkyl ether acetic acid, N-acyl amino acid in which a hydrogen atom of the amino group may be substituted with a substituent, polyoxyethylene alkyl ether phosphoric acid, polyoxyethylene polycyclic phenyl ether phosphoric acid, alkyl phosphoric acid, and salts thereof; and the reagents for measuring hydrogen peroxide, respectively, as mentioned above.

The reagent for measuring glycated hemoglobin of the present invention may be in a freeze-dried state or in a state of being dissolved in an aqueous medium. Examples of the aqueous medium include the aqueous medium as mentioned above. In a case where a reagent in a freeze-dried state is used to measure glycated hemoglobin in a hemoglobin-containing sample, the reagent is dissolved in an aqueous medium and used.

In the reagent for measuring glycated hemoglobin of the present invention, the content of the enzyme that catalyzes a reaction of oxidizing glycated hemoglobin to generate hydrogen peroxide is usually such a content that the concentration in a state of being dissolved in an aqueous medium can be 0.1 to 30 kU/L, with such a content that the concentration can be 0.2 to 15 kU/L being preferred.

In the reagent for measuring glycated hemoglobin of the present invention, the content of the at least one anionic surfactant selected from the group consisting of N-acyl taurine in which a hydrogen atom of the amino group may be substituted with a substituent, alkyl sulfoacetic acid, polyoxyethylene alkyl ether acetic acid, N-acyl amino acid in which a hydrogen atom of the amino group may be substituted with a substituent, polyoxyethylene alkyl ether phosphoric acid, polyoxyethylene polycyclic phenyl ether phosphoric acid, alkyl phosphoric acid, and salts thereof is such a content that the concentration in a state of being dissolved in an aqueous medium can be 0.001% to 10%, with such a content that the concentration can be 0.01% to 5% being preferred.

The measuring reagent of the present invention may contain, as necessary, an aqueous medium, a stabilizer, an antiseptic, a salt, an interference substance elimination agent, an organic solvent, and the like. Examples of the aqueous medium include the aqueous medium as mentioned above. Examples of the stabilizer include ethylenediaminetetraacetic acid (EDTA), sucrose, calcium chloride, calcium acetate, calcium nitrate, potassium ferrocyanide, bovine serum albumin (BSA), a polyoxyethylene nonionic surfactant such as polyoxyethylene alkyl phenyl ether, glycerin, and alkylene glycol. Examples of the alkylene glycol include ethylene glycol and propylene glycol. Examples of the antiseptic include sodium azide and antibiotics. Examples of the salt include sodium chloride, sodium nitrate, sodium sulfate, sodium carbonate, sodium formate, sodium acetate, potassium chloride, potassium nitrate, potassium sulfate, potassium carbonate, potassium formate, and potassium acetate. Examples of the interference substance elimination agent include ascorbic acid oxidase for eliminating influence of ascorbic acid. Examples of the organic solvent include dimethylformamide (DMF), dimethylsulfoxide (DMSO), dioxane, acetone, methanol, and ethanol as an auxiliary agent for dissolution of a leuco-type chromogen in an aqueous medium.

(3) Kit for measuring glycated hemoglobin in hemoglobin-containing sample

The reagent for measuring glycated hemoglobin in a hemoglobin-containing sample of the present invention may be stored, distributed, and used in the form of a kit. The kit for measuring glycated hemoglobin in a hemoglobin-containing sample of the present invention is used in the method for measuring glycated hemoglobin in a hemoglobin-containing sample of the present invention. Examples of the measuring kit of the present invention include a kit of a two-reagent system and a kit of a three-reagent system, with a kit of a two-reagent system being preferred.

In the present invention, in a case where the kit of a two-reagent system is used to measure glycated hemoglobin in a hemoglobin-containing sample, for example, the glycated hemoglobin can be measured by adding the hemoglobin-containing sample and a first reagent to a reaction cuvette to carry out a reaction at a predetermined temperature for a predetermined time, and then adding a second reagent, and measuring the generated hydrogen peroxide.

Kit 1

A kit containing:

a first reagent which comprises at least one anionic surfactant selected from the group consisting of N-acyl taurine in which a hydrogen atom of the amino group may be substituted with a substituent, alkyl sulfoacetic acid, polyoxyethylene alkyl ether acetic acid, N-acyl amino acid in which a hydrogen atom of the amino group may be substituted with a substituent, polyoxyethylene alkyl ether phosphoric acid, polyoxyethylene polycyclic phenyl ether phosphoric acid, alkyl phosphoric acid, and salts thereof; and a second reagent which comprises an enzyme that catalyzes a reaction of oxidizing glycated hemoglobin to generate hydrogen peroxide.

Kit 2

A kit containing:

a first reagent which comprises at least one anionic surfactant selected from the group consisting of N-acyl taurine in which a hydrogen atom of the amino group may be substituted with a substituent, alkyl sulfoacetic acid, polyoxyethylene alkyl ether acetic acid, N-acyl amino acid in which a hydrogen atom of the amino group may be substituted with a substituent, polyoxyethylene alkyl ether phosphoric acid, polyoxyethylene polycyclic phenyl ether phosphoric acid, alkyl phosphoric acid, and salts thereof; and a second reagent which comprises an enzyme that catalyzes a reaction of oxidizing glycated hemoglobin to generate hydrogen peroxide, in which a reagent for measuring hydrogen peroxide is contained in either or both of the first reagent and the second reagent.

In a case where a reagent comprising a peroxidase and a leuco-type chromogen is used as the reagent for measuring hydrogen peroxide, the peroxidase and the leuco-type chromogen are preferably comprised in separate reagents. That is, it is preferable that the peroxidase and the leuco-type chromogen are comprised in the first reagent and the second reagent, respectively, or in the second reagent and the first reagent, respectively.

Kit 3

A kit containing:

a first reagent which comprises an enzyme that catalyzes a reaction of oxidizing glycated hemoglobin to generate hydrogen peroxide; and a second reagent which comprises at least one anionic surfactant selected from the group consisting of N-acyl taurine in which a hydrogen atom of the amino group may be substituted with a substituent, alkyl sulfoacetic acid, polyoxyethylene alkyl ether acetic acid, N-acyl amino acid in which a hydrogen atom of the amino group may be substituted with a substituent, polyoxyethylene alkyl ether phosphoric acid, polyoxyethylene polycyclic phenyl ether phosphoric acid, alkyl phosphoric acid, and salts thereof.

Kit 4

A kit containing:

a first reagent which comprises an enzyme that catalyzes a reaction of oxidizing glycated hemoglobin to generate hydrogen peroxide; and a second reagent which comprises at least one anionic surfactant selected from the group consisting of N-acyl taurine in which a hydrogen atom of the amino group may be substituted with a substituent, alkyl sulfoacetic acid, polyoxyethylene alkyl ether acetic acid, N-acyl amino acid in which a hydrogen atom of the amino group may be substituted with a substituent, polyoxyethylene alkyl ether phosphoric acid, polyoxyethylene polycyclic phenyl ether phosphoric acid, alkyl phosphoric acid, and salts thereof, in which a reagent for measuring hydrogen peroxide is comprised in either or both of the first reagent and the second reagent.

In a case where a reagent comprising a peroxidase and a leuco-type chromogen is used as the reagent for measuring hydrogen peroxide, each of the peroxidase and the leuco-type chromogen is preferably comprised separately. That is, it is preferable that the peroxidase and the leuco-type chromogen are comprised in the first reagent and the second reagent, respectively, or in the second reagent and the first reagent, respectively.

Kit 5

A kit containing:

a first reagent which comprises an enzyme that catalyzes a reaction of oxidizing glycated hemoglobin to generate hydrogen peroxide, and at least one anionic surfactant selected from the group consisting of N-acyl taurine in which a hydrogen atom of the amino group may be substituted with a substituent, alkyl sulfoacetic acid, polyoxyethylene alkyl ether acetic acid, N-acyl amino acid in which a hydrogen atom of the amino group may be substituted with a substituent, polyoxyethylene alkyl ether phosphoric acid, polyoxyethylene polycyclic phenyl ether phosphoric acid, alkyl phosphoric acid, and salts thereof; and a second reagent which comprises a reagent for measuring hydrogen peroxide.

Kit 6

A kit containing:

a first reagent which comprises an enzyme that catalyzes a reaction of oxidizing glycated hemoglobin to generate hydrogen peroxide, at least one anionic surfactant selected from the group consisting of N-acyl taurine in which a hydrogen atom of the amino group may be substituted with a substituent, alkyl sulfoacetic acid, polyoxyethylene alkyl ether acetic acid, N-acyl amino acid in which a hydrogen atom of the amino group may be substituted with a substituent, polyoxyethylene alkyl ether phosphoric acid, polyoxyethylene polycyclic phenyl ether phosphoric acid, alkyl phosphoric acid, and salts thereof, and a reagent for measuring hydrogen peroxide; and a second reagent which comprises a reagent for measuring hydrogen peroxide.

In a case where a reagent comprising a peroxidase and a leuco-type chromogen is used as the reagent for measuring hydrogen peroxide, each of the peroxidase and the leuco-type chromogen is preferably comprised separately. That is, it is preferable that the peroxidase and the leuco-type chromogen are comprised in the first reagent and the second reagent, respectively, or in the second reagent and the first reagent, respectively.

Kit 7

A kit containing:

a first reagent which comprises a reagent for measuring hydrogen peroxide; and a second reagent which comprises an enzyme that catalyzes a reaction of oxidizing glycated hemoglobin to generate hydrogen peroxide, and at least one anionic surfactant selected from the group consisting of N-acyl taurine in which a hydrogen atom of the amino group may be substituted with a substituent, alkyl sulfoacetic acid, polyoxyethylene alkyl ether acetic acid, N-acyl amino acid in which a hydrogen atom of the amino group may be substituted with a substituent, polyoxyethylene alkyl ether phosphoric acid, polyoxyethylene polycyclic phenyl ether phosphoric acid, alkyl phosphoric acid, and salts thereof.

Kit 8

A kit containing:

a first reagent which comprises a reagent for measuring hydrogen peroxide; and a second reagent which comprises an enzyme that catalyzes a reaction of oxidizing glycated hemoglobin to generate hydrogen peroxide, at least one anionic surfactant selected from the group consisting of N-acyl taurine in which a hydrogen atom of the amino group may be substituted with a substituent, alkyl sulfoacetic acid, polyoxyethylene alkyl ether acetic acid, N-acyl amino acid in which a hydrogen atom of the amino group may be substituted with a substituent, polyoxyethylene alkyl ether phosphoric acid, polyoxyethylene polycyclic phenyl ether phosphoric acid, alkyl phosphoric acid, and salts thereof, and a reagent for measuring hydrogen peroxide.

In a case where a reagent comprising a peroxidase and a leuco-type chromogen is used as the reagent for measuring hydrogen peroxide, each of the peroxidase and the leuco-type chromogen is preferably comprised separately. That is, it is preferable that the peroxidase and the leuco-type chromogen are comprised in the first reagent and the second reagent, respectively, or in the second reagent and the first reagent, respectively.

The kit for measuring glycated hemoglobin of the present invention may be in a freeze-dried state or in a state of being dissolved in an aqueous medium. Examples of the aqueous medium include the aqueous medium as mentioned above. In a case where a kit in a freeze-dried state is used to measure glycated hemoglobin in a hemoglobin-containing sample, reagents comprised of the kit are dissolved in an aqueous medium and used.

In the reagents comprised of the measuring kit of the present invention, the content of the enzyme that catalyzes a reaction of oxidizing glycated hemoglobin to generate hydrogen peroxide is usually such a content that the concentration in a state of being dissolved in an aqueous medium can be 0.2 to 60 kU/L, with such a content that the concentration can be 0.4 to 30 kU/L being preferred.

In the reagents comprised of the measuring kit of the present invention, the content of the at least one anionic surfactant selected from the group consisting of N-acyl taurine in which a hydrogen atom of the amino group may be substituted with a substituent, alkyl sulfoacetic acid, polyoxyethylene alkyl ether acetic acid, N-acyl amino acid in which a hydrogen atom of the amino group may be substituted with a substituent, polyoxyethylene alkyl ether phosphoric acid, polyoxyethylene polycyclic phenyl ether phosphoric acid, alkyl phosphoric acid, and salts thereof is usually such a content that the concentration in a state of being dissolved in an aqueous medium can be 0.002% to 20%, with such a content that the concentration can be 0.02% to 10% being preferred.

EXAMPLES

[0078] Hereinafter, the present invention will be described in more detail with reference to examples, but these examples do not limit a scope of the present invention in any way. In the present examples, comparative examples, and reference examples, reagents and enzymes of the following manufacturers were used.

Bis-Tris (manufactured by Dojindo Molecular Technologies, Inc.), DA-67 (manufactured by Wako Pure Chemical Industries, Ltd.), 4-aminoantipyrine (manufactured by Actec), EMSE (manufactured by Dojindo Molecular Technologies, Inc.), peroxidase (manufactured by Toyobo Co., Ltd.), fructosyl valine (prepared by the method described in J. Agric. Food Chem., Vol. 24, No. 1, pp. 70 to 73 (1976))

NIKKOL LMT [N-acyl taurine salt (sodium N-lauroyl-N-methyl taurine); manufactured by Nikko Chemicals Co., Ltd.]

NIKKOL PMT [N-acyl taurine salt (sodium N-palmitoyl-N-methyl taurine); manufactured by Nikko Chemicals Co., Ltd.]

NIKKOL LSA-F [alkyl sulfoacetic acid salt (sodium lauryl sulfoacetate); manufactured by Nikko Chemicals Co., Ltd.] NIKKOL AKYPO RLM 45 NV [polyoxyethylene alkyl ether acetic acid salt (sodium polyoxyethylene lauryl ether acetate); manufactured by Nikko Chemicals Co., Ltd.]

NIKKOL ALANINATE LN-30 [N-acyl amino acid salt (sodium N-lauroyl-N-methyl-β-alanine); manufactured by Nikko Chemicals Co., Ltd.]

NIKKOL SARCOSINATE PN [N-acyl amino acid salt (sodium N-palmitoyl sarcosine); manufactured by Nikko Chemicals Co., Ltd.]

PLYSURF A212C [polyoxyethylene alkyl ether phosphoric acid (polyoxyethylene tridecyl ether phosphoric acid); manufactured by DKS Co., Ltd.]

PLYSURF AL [polyoxyethylene polycyclic phenyl ether phosphoric acid (polyoxyethylene styrenated phenyl ether phosphoric acid); manufactured by DKS Co., Ltd.]

NIKKOL SLP-N [alkyl phosphoric acid salt (sodium lauryl phosphate); manufactured by Nikko Chemicals Co., Ltd.)]

NEOGEN POWDER W (linear alkylbenzene sulfonic acid; manufactured by DKS Co., Ltd.)

NIKKOL SLS (sodium lauryl sulfate; manufactured by Nikko Chemicals Co., Ltd.)

NIKKOL OS-14 (sodium α-olefin sulfonate; manufactured by Nikko Chemicals Co., Ltd.)

NIKKOL SBL-2N-27 (polyoxyethylene alkyl ether sulfate; manufactured by Nikko Chemicals Co., Ltd.)

NONSAL LK-2 (alkyl metal salt of natural fatty acid; manufactured by NOF CORPORATION)

Glycerin (manufactured by Wako Pure Chemical Industries, Ltd.)

Ethylene glycol (manufactured by Junsei Chemical Co., Ltd.)

Propylene glycol (manufactured by Junsei Chemical Co., Ltd.)

n-Dodecyl-β-maltoside (nonionic surfactant; manufactured by Wako Pure Chemical Industries, Ltd.)

Polyoxyethylene cetyl ether (Brij 58; manufactured by Sigma-Aldrich)

Tetradecyl trimethylammonium bromide (C14 TMA) (cationic surfactant; manufactured by Tokyo Chemical Industry Co., Ltd.)

Hexadecyl trimethylammonium bromide (C16 TMA) (cationic surfactant; manufactured by Tokyo Chemical Industry Co., Ltd.)

[Reference Example 1] Construction of FPDX-47Δ3

(1) Construction of FPDX-47 Expression Vector pTrc-FPDX-47

PCR was carried out using an expression plasmid pTrc-FPDX-42 containing a DNA consisting of a base sequence represented by SEQ ID NO: 1 as a template DNA, FPDX-42 F342V-F consisting of a base sequence represented by SEQ ID NO: 2 and FPDX-42 F342V-R consisting of a base sequence represented by SEQ ID NO: 3 as a forward primer and a reverse primer, respectively, with the following reagent composition and under the following PCR condition to obtain a PCR product. pTrc-FPDX-42 is an expression plasmid containing DNA encoding FPDX-42, which is an enzyme that catalyzes a reaction of oxidizing glycated hemoglobin to generate hydrogen peroxide, and can be constructed according to a method disclosed in PCT International Publication No. WO2015/005258. PCR was carried out based on a protocol of DNA polymerase "KOD-Plus-", which is a PCR kit manufactured by Toyobo Co., Ltd.

(Reagent composition)
KOD-Plus-buffer
Template DNA (pTrc-FPDX-42) 1 to 2 ng/μL
Forward primer (FPDX-42 F342V-F) 0.3 μmol/L
Reverse primer (FPDX-42 F342V-R) 0.3 μmol/L
dNTP mixed solution 0.2 mmol/L each
$MgSO_4$ 1 mmol/L
DNA polymerase (KOD-Plus-) 0.02 U/μL
Sterile water was added to make 50 μL.
(PCR Condition)
1. 94° C. 2 minutes
2. 98° C. 15 seconds
3. 60° C. 30 seconds
4. 68° C. 6 minutes
5. Repeat of 2 to 4 (all 30 cycles)
6. 68° C. 10 minutes 1 μL of "restriction enzyme Dpn I" manufactured by New England Biolabs, Inc. was added to 50 μL of the obtained PCR product, and incubation was carried out at 37° C. for 1 hour to decompose the template DNA. The PCR product which had been subjected to the restriction enzyme treatment was purified using "Wizard SV Gel and PCR Clean-Up System" manufactured by Promega according to a protocol of the kit to obtain a purified sample of the PCR product.

Subsequently, the purified sample of the obtained PCR product was used to transform an E. coli competent cell "Competent high DH 5α" manufactured by Toyobo Co., Ltd. Colonies grown on an LB agar medium containing 50 mg/L ampicillin were selected and plasmids were extracted using "Wizard Plus SV Minipreps DNA Purification" manufactured by Promega according to a protocol of the kit.

By performing sequence analysis of the extracted plasmids with a DNA sequencer, it was identified whether a plasmid pTrc-FPDX-47 that contains DNA having a base sequence represented by SEQ ID NO: 4 which encodes FPDX-47 was constructed. For the sequence analysis, pTrc-F consisting of a base sequence represented by SEQ ID NO: 5 and pTrc-R consisting of a base sequence represented by SEQ ID NO: 6 which reflect base sequences immediately before and after a multiple cloning site of a pTrc99a vector (manufactured by GE Healthcare Bioscience), respectively were used as a forward primer and a reverse primer, respectively.

(2) Construction of FPDX-47Δ3-Expressing Vector pTrc-FPOX-47Δ3

FPDX-47Δ3-R consisting of a base sequence represented by SEQ ID NO: 7 which had been obtained by removing 9 bases positioned immediately before a termination codon at a 3' end of a base sequence encoding FPDX-47 contained in the plasmid pTrc-FPDX-47 and adding a termination codon and a Bam HI restriction enzyme recognition site, and pTrc-F consisting of a base sequence represented by SEQ ID NO: 5 which reflects a base sequence immediately before the multiple cloning site of pTrc99a vector were designed and chemically synthesized.

Using pTrc-F and FPDX-47Δ3-R as a primer pair, PCR was carried out using pTrc-FPDX-47 as a template with the following reagent composition and PCR condition, to obtain a PCR product which contains a DNA fragment containing a base sequence that encodes a deletion variant, FPDX-47Δ3 in which three amino acids at a C terminus of FPDX-47 are deleted. PCR was carried out based on a protocol of DNA polymerase "KOD-Plus-", which is a PCR kit manufactured by Toyobo Co., Ltd.

(Reagent Composition)
KOD-Plus-buffer
Template DNA (pTrc-FPDX-47) 0.2 to 0.5 ng/μL
Forward primer (pTrc-F) 0.3 μmol/L
Reverse primer (FPDX-47Δ3-R) 0.3 μmol/L
dNTP mixed solution 0.2 mmol/L each
MgSO$_4$ 1 mmol/L
DNA polymerase (KOD-Plus-) 0.02 U/μL
Sterile water was added to make 50 μL.
(PCR Condition)
1. 94° C. 2 minutes
2. 98° C. 15 seconds
3. 60° C. 30 seconds
4. 68° C. 2 minutes
5. Repeat of 2 to 4 (all 30 cycles)
6. 68° C. for 5 minutes Using a portion of the obtained PCR product, electrophoresis was carried out on a 1% agarose TAE gel to identify whether a DNA fragment of an assumed size was obtained.

The obtained PCR product was purified using "Wizard SV Gel and PCR Clean-Up system" manufactured by Promega according to a protocol of the kit, to obtain a DNA fragment that contains DNA encoding FPOX-47Δ3. The DNA fragment thus obtained was treated with two types of restriction enzymes Nco I and Bam HI (both manufactured by Takara Bio Inc.) at 37° C. for 1 hour, and the obtained reaction mixture was purified using "Wizard SV Gel and PCR Clean-Up System" manufactured by Promega according to a protocol of the kit, to obtain a restriction enzyme-treated fragment.

In addition, pTrc-FPDX-15 expressing a glycated peptide oxidase FPDX-15 which has no activity of oxidizing fructosyl hexapeptide and is described in PCT International Publication No. WO2010/041715 was similarly treated with the same restriction enzymes, electrophoresis was carried out on a 1% agarose TAE gel, a DNA fragment corresponding to the vector was excised, and the DNA fragment was purified using Wizard SV Gel and PCR Clean-Up system, to obtain a plasmid fragment from which DNA encoding FPDX-15 was removed.

The obtained restriction enzyme-treated fragment was mixed with the plasmid fragment from which DNA encoding FPDX-15 was removed, ligation was carried out using a DNA Ligation Kit (manufactured by Takara Bio Inc.), and then the ligation product was introduced into an *E. coli* competent cell "Competent high DH5α" manufactured by Toyobo Co., Ltd.

The *E. coli* into which the ligation product had been introduced was inoculated on an LB agar medium containing 50 mg/L ampicillin, cultured at 37° C. for 14 hours, and emerging colonies were selected. The selected colonies were cultured in an LB liquid medium containing 50 mg/L ampicillin at 37° C. for 14 hours and plasmids were prepared using "Wizard Plus S V Minipreps DNA Purification" manufactured by Promega according to a protocol of the kit. PCR was carried out using pTrc-F consisting of a base sequence represented by SEQ ID NO: 5 and pTrc-R consisting of a base sequence represented by SEQ ID NO: 6 as a forward primer and a reverse primer, respectively, to identify a base sequence of each of the prepared plasmids and identify whether a base sequence represented by SEQ ID NO: 8 in which nine bases on a 3' side except a termination codon in the base sequence of FPDX-47 were deleted was contained on the plasmid. This plasmid is called pTrc-FPOX-47Δ3.

(3) Acquisition of FPDX-47Δ3

*E. coli* containing pTrc-FPOX-47Δ3 obtained in the above (2) was shake-cultured in an LB medium containing 50 mg/L ampicillin at 37° C. for 14 hours. Purification of the obtained culture solution was carried out according to the purification method of glycated peptide oxidases FPDX-9 and FPDX-15 described in PCT International Publication No. WO 2010/041715, to obtain a solution of purified FPDX-47Δ3. An amino acid sequence of FPDX-47 and an amino acid sequence of FPDX-47Δ3 are shown in SEQ ID NO: 9 and SEQ ID NO: 10, respectively.

(4) Identification of Enzyme Activity (Hereinafter Referred to as Glycated Hemoglobin Oxidase Activity) of FPOX-47Δ3 that Catalyzes a Reaction of Oxidizing Glycated Hemoglobin to Generate Hydrogen Peroxide A glycated hemoglobin oxidase activity of FPDX-47Δ3 toward HbA1c was identified by using the solution of purified FPDX-47Δ3 obtained in the above (3) with the following measuring kit and measuring procedure.

<Measuring Kit A>
First Reagent
Bis-Tris (pH 6.5) 50 mmol/L
DA-67 40 μmol/L
NIKKOL LMT 1 g/L
Second Reagent
Phosphate buffer solution (pH 6.5) 10 mmol/L
FPDX-47Δ3 1.5 kU/L
Peroxidase 200 kU/L
<Measuring Kit a>
First Reagent
Bis-Tris (pH 6.5) 50 mmol/L
DA-67 40 μmol/L
Second Reagent
Phosphate buffer solution (pH 6.5) 10 mmol/L
FPDX-47Δ3 1.5 kU/L
Peroxidase 200 kU/L The measuring kit a is the same as the measuring kit A except that NIKKOL LMT is not comprised in the first reagent.

<Sample>
Hemolyzed samples prepared by dilution of blood cells obtained by centrifugation of human blood with deionized water to hemolyze, and with the HbA1c concentrations of 2.6 μmol/L, 4.5 μmol/L, 6.4 μmol/L, 8.4 μmol/L determined from both of the KO500 method, which is a standard method for measuring HbA1c, and the SLS-hemoglobin method, which is one of methods for measuring a total hemoglobin, were used as samples.

<Measuring Procedure>

Each of the above-mentioned samples (10 µL) and the first reagent (100 µL) of the above-mentioned measuring kit A were added to a reaction cuvette, a reaction was carried out at 37° C. for 5 minutes (first reaction), and an absorbance (E1) of the reaction solution was measured at a main wavelength of 660 nm and a sub-wavelength of 800 nm. Subsequently, the second reagent (40 µL) of the above-mentioned measuring kit A was added to the reaction solution, a further reaction was carried out at 37° C. for 5 minutes (second reaction), and an absorbance (E2) of the reaction solution was measured at a main wavelength of 660 nm and a sub-wavelength of 800 nm. E1 was subtracted from E2 to calculate an absorbance difference $\Delta E'_A$.

Each of the above-mentioned samples (10 µL) and the first reagent (100 µL) of the above-mentioned measuring kit a were added to a reaction cuvette, a reaction was carried out at 37° C. for 5 minutes (first reaction), and an absorbance (E3) of the reaction solution was measured at a main wavelength of 660 nm and a sub-wavelength of 800 nm. Subsequently, the second reagent (40 µL) of the above-mentioned measuring kit a was added to the reaction solution, a further reaction was carried out at 37° C. for 5 minutes (second reaction), and an absorbance (E4) of the reaction solution was measured at a main wavelength of 660 nm and a sub-wavelength of 800 nm. E3 was subtracted from E4 to calculate an absorbance difference $\Delta E'_a$.

$\Delta E'_a$ was subtracted from $\Delta E'_A$ to afford an absorbance difference $\Delta E$ for each sample. A relationship between an HbA1c concentration and $\Delta E$ in each of the samples is shown in FIG. 1.

As is apparent from FIG. 1, in the measurement using a kit (kit A) of the present invention comprising N-acyltaurine, which is an anionic surfactant, a quantitative relationship was recognized between an HbA1c concentration and an absorbance. Accordingly, it was identified that FPDX-47Δ3 is an enzyme having the activity that catalyzes a reaction of oxidizing glycated hemoglobin to generate hydrogen peroxide.

Example 1

HbA1c measuring kits (kit 1A to 1I) comprising the following first reagent and second reagent were prepared.

First Reagent
Bis-Tris (pH 6.5) 50 mmol/L
DA-67 40 µmol/L
Surfactants A to I (see Table 1)
Second Reagent
Phosphate buffer solution (pH 6.5) 10 mmol/L
FPOX-47Δ3 0.9 kU/L
Peroxidase 200 kU/L Comparative Example 1

HbA1c measuring kits (kits 1a to 1e) comprising the following first reagent and second reagent were prepared.

First Reagent
Bis-Tris (pH 6.5) 50 mmol/L
DA-67 40 µmol/L
Surfactants a to e (see Table 1)
Second Reagent
Phosphate buffer solution (pH 6.5) 10 mmol/L
FPOX-47Δ3 0.9 kU/L
Peroxidase 200 kU/L
Surfactants a to e are the anionic surfactants described in PCT International Publication No. WO2015/060429.

Example 2

Using the kit 1A of Example 1 as a kit for measuring HbA1c, and 6 concentrations of whole blood in which HbA1c concentrations were determined to be 4.9%, 5.6%, 6.7%, 7.5%, 8.4%, and 9.9%, respectively, by the KO500 method, which is an HPLC method, as samples, a proportion [HbA1c (%)] of HbA1c concentration (amount) to total hemoglobin concentration (amount) in each of the samples was determined by the following procedure.

(1) Preparation of Calibration Curve for Determination of Total Hemoglobin Concentration Using hemoglobin B-test Wako, which is a kit for measuring total hemoglobin (SLS-hemoglobin method) (manufactured by Wako Pure Chemical Industries, Ltd.), and a standard product (total hemoglobin concentration: 15.3 mg/mL) attached to the hemoglobin B-test Wako, measurement was carried out according to the following procedure, and an absorbance for the standard product was measured.

The standard product (10 µL) and the hemoglobin B-test Wako (250 µL) were added to a reaction cuvette to carry out a reaction at 37° C. for 10 minutes. An absorbance (E) of the reaction solution was measured at a main wavelength of 546 nm and a sub-wavelength of 660 nm to afford an absorbance for the standard product. Measurement was carried out by the same method except that a physiological saline was used in place of the standard product to afford an absorbance for the physiological saline. The absorbance for the physiological saline was subtracted from the absorbance for the standard product to afford a blank-corrected absorbance for the standard product. Based on the blank-corrected absorbance for the standard product and a blank-corrected absorbance (0 Abs) for the physiological saline, a calibration curve showing a relationship between a total hemoglobin concentration (µmol/L) and an absorbance was prepared.

(2) Preparation of Calibration Curve for Determination of HbA1c Concentration

For two blood cell fractions in which HbA1c concentrations were determined to be 2.98 µmol/L and 6.13 µmol/L by the KO500 method, an absorbance for each of the blood cell fractions was measured using the HbA1c measuring kit 1A of Example 1 according to the following procedure.

Each of the above-mentioned blood cell fractions (10 µL) and the first reagent (100 µL) of the kit 1A of Example 1 were added to a reaction cuvette, a reaction was carried out at 37° C. for 5 minutes (first reaction), and an absorbance (E1) of the reaction solution was measured at a main wavelength of 660 nm and a sub-wavelength of 800 nm. Subsequently, the second reagent (40 µL) of the kit 1A of Example 1 was added to the reaction solution, a further reaction was carried out at 37° C. for 5 minutes (second reaction), and an absorbance (E2) of the reaction solution was measured at a main wavelength of 660 nm and a sub-wavelength of 800 nm. E1 was subtracted from E2 to calculate an absorbance difference $\Delta E'_{1A}$, and this was taken as an absorbance for each blood cell fraction. An absorbance difference $\Delta E'_{physiological\ saline}$ was calculated by the same method except that a physiological saline was used in place of each of the above-mentioned blood cell fractions, and this was taken as an absorbance for the physiological saline. The absorbance for the physiological saline was subtracted from the absorbance for each of the blood cell fractions to afford a blank-corrected absorbance for the blood cell fraction. Based on the blank-corrected absorbance for the blood cell fraction and a blank-corrected absorbance (0 Abs) for the physiological saline, a calibration curve showing a relationship between an HbA1c concentration (μmol/L) and an absorbance was prepared.

(3) Determination of Total Hemoglobin Concentration in Each Blood Cell Fraction

For each of the samples, centrifugation was carried out at 3,000 rpm (1500×G) at 25° C. for 5 minutes to obtain a blood cell fraction. For each of the blood cell fractions, measurement was carried out by the same method as in (1) by using hemoglobin B-test Wako, and a total hemoglobin concentration (μmol/L) in each of the blood cell fractions was determined based on the obtained measurement value and the calibration curve of (1).

(4) Determination of HbA1c Concentration in Each Blood Cell Fraction

For each of the blood cell fractions obtained in (3), measurement was carried out by the same method as in (2) using the measuring kit 1A of the present invention, and an HbA1c concentration (μmol/L) in each of the blood cell fractions was determined based on the obtained measurement value and the calibration curve of (2).

(5) Determination of HbA1c (%) (Proportion of HbA1c Concentration to Total Hemoglobin Concentration)

Based on the total hemoglobin concentration (μmol/L) in each of the blood cell fractions determined in the above (3) and the HbA1c concentration (μmol/L) in each of the blood cell fractions determined in the above (4), HbA1c (%) was calculated as an NGSP value (international standard value) by the following Expression (II).

HbA1c (%)=[HbA1c concentration (μmol/L)]/[total hemoglobin concentration (μmol/L)]×98.2+1.97  (II)

(6) Determination of HbA1c (%) in Same Blood Cell Fraction by KO500 Method

Using the same blood cell fraction as the blood cell fraction used for determining HbA1c (%) in the above (5), HbA1c (%) in each of the blood cell fractions was determined by the KO500 method, which is an HPLC method.

(7) Correlation Between Measuring Method of Present Invention and KO500 Method

Based on the HbA1c (%) determined in the above (5) using the measuring method of the present invention and the HbA1c (%) determined in the above (6) using the KO500 method, a correlation between the measuring method of the present invention and the KO500 method was verified to afford a correlation coefficient.

As a result, the correlation coefficient between both the measurement methods was 0.943 to afford a good correlation between both the measurement methods. Accordingly, it proved that HbA1c in a sample can be accurately measured by the measuring method of the present invention using the kit 1A of Example 1. HbA1c (%) in each of the samples was determined by using the same procedure as above except that each of the kits 1B, 1C, 1D, 1E, 1F, 1G, 1H, and 1I of Example 1 was used in place of the kit 1A of Example 1, and a correlation between the measuring method using each kit of the kits 1B, 1C, 1D, 1E, 1F, 1G, 1H, and 1I, and the KO500 method was verified to afford a correlation coefficient. The results are shown in Table 1.

Comparative Example 2

HbA1c (%) in each of the blood cell fractions was determined by the same procedure as in Example 2 except that each kit of the kits 1a, 1b, 1c, 1d, and 1e of Comparative Example 1 was used in place of the kit 1A of Example 1, and a correlation between the measuring method using each kit of the kits 1a, 1b, 1c, 1d, and 1e, and the KO500 method was verified to afford a correlation coefficient. The results are shown in Table 1.

TABLE 1

| | Anionic surfactant | | |
|---|---|---|---|
| Kit | Product name (concentration) | Type | Correlation coefficient* |
| 1A | NIKKOL LMT (1 g/L) | N-Acyl taurine salt | 0.943 |
| 1B | NIKKOL PMT (0.5 g/L) | N-Acyl taurine salt | 0.923 |
| 1C | NIKKOL LSA-F (0.5 g/L) | Alkyl sulfoacetic acid salt | 0.916 |
| 1D | NIKKOL AKYPO RLM 45 NV (5 g/L) | Polyoxyethylene alkyl ether acetic acid salt | 0.947 |
| 1E | NIKKOL ALANIATE LN-30 (5 g/L) | N-Acyl amino acid salt | 0.992 |
| 1F | NIKKOL SARCOSINATE PN (0.5 g/L) | N-Acyl amino acid salt | 0.963 |
| 1G | PLYSURF AL (5 g/L) | Polyoxyethylene polycyclic phenyl ether phosphoric acid | 0.973 |
| 1H | PLYSURF A212C (2 g/L) | Polyoxyethylene alkyl ether phosphoric acid | 0.999 |
| 1I | NIKKOL SLP-N (0.5 g/L) | Alkyl phosphoric acid | 0.989 |
| 1a | NEOGEN POWDER W (2 g/L) | Linear alkylbenzene sulfonic acid | −0.598 |
| 1b | NIKKOL SLS (0.5 g/L) | Alkyl sulfate | −0.702 |
| 1c | NIKKOL OS-14 (1 g/L) | α-Olefin sulfonic acid | 0.326 |
| 1d | NIKKOL SBL-2N-27 (2.5 g/L) | Polyoxyethylene alkyl ether sulfate | −0.481 |
| 1e | NONSAL LK-2 (0.25 g/L) | Alkyl metal salt of natural fatty acid | −0.445 |

*Correlation coefficient: Correlation coefficient relating to a correlation with the KO500 method As is apparent from Table 1, in the measurement using the kits 1A to 1I of the present invention, a good correlation with the KO500 method was recognized. However, in the measurement using the kits 1a to 1e of the Comparative Example 1, a good correlation was not recognized with the KO500 method. Accordingly, it proved that glycated hemoglobin in a sample can be accurately measured by using the kits 1A to 1I of the present invention.

Example 3

HbA1c measuring kits (kits 2A to 2I) comprising the following first reagent and second reagent were prepared.

First Reagent

Bis-Tris (pH 6.5) 50 mmol/L

DA-67 40 μmol/L

Surfactants A to I (see Table 2)

Second Reagent

Phosphate buffer solution (pH 6.5) 10 mmol/L

FPOX-47Δ3 1.5 kU/L

Peroxidase 200 kU/L

Each of the kits (kits 2A to 2I) of Example 3 was the same as each of the kits (kit 1A to 1I) of Example 1 except that FPDX-47Δ3 in the second reagent was 1.5 kU/L.

Comparative Example 3

HbA1c measuring kits (kits 2a to 2e) comprising the following first reagent and second reagent were prepared.
First Reagent
Bis-Tris (pH 6.5) 50 mmol/L
DA-67 40 µmol/L
Surfactants a to e (see Table 2)
Second Reagent
Phosphate buffer solution (pH 6.5) 10 mmol/L
FPOX-47Δ3 1.5 kU/L
Peroxidase 200 kU/L
Surfactants a to e are the anionic surfactants described in PCT International Publication No. WO2015/060429. Each of the kits (kit 2a to 2e) of Comparative Example 3 was the same as each of the kits (kit 1a to 1e) of Comparative Example 1 except that FPDX-47Δ3 in the second reagent was 1.5 kU/L.

Example 4

Using the kit 2A of Example 3 as a kit for measuring HbA1c, and 6 concentrations of whole blood in which HbA1c concentrations were determined to be 4.9%, 5.6%, 6.7%, 7.5%, 8.4%, and 9.9%, respectively, by the KO500 method, which is an HPLC method, as samples, a proportion [HbA1c (%)] of HbA1c concentration (amount) to total hemoglobin concentration (amount) in each of the samples was determined by the following procedure.

(1) Preparation of Calibration Curve for Determination of Total Hemoglobin Concentration Using hemoglobin B-test Wako, which is a kit for measuring total hemoglobin (SLS-hemoglobin method) (manufactured by Wako Pure Chemical Industries, Ltd.), measurement was carried out in the same manner as in (1) of Example 2, and a calibration curve showing a relationship between a total hemoglobin concentration and an absorbance was prepared.

(2) Preparation of Calibration Curve for Determination of HbA1c Concentration

For two blood cell fractions in which HbA1c concentrations were determined to be 2.54 µmol/L and 6.40 µmol/L by the KO500 method, measurement was carried out in the same manner as in (2) of Example 2 using the HbA1c measuring kit 2A of Example 3, and an absorbance for each of the blood cell fractions was measured. Similar measurement was carried out using a physiological saline in place of the blood cell fraction, and an absorbance for the physiological saline was measured. The absorbance for the physiological saline was subtracted from the absorbance for each of the blood cell fractions to afford a blank-corrected absorbance for the blood cell fraction. Based on the blank-corrected absorbance for the blood cell fraction and a blank-corrected absorbance (0 Abs) for the physiological saline, a calibration curve showing a relationship between an HbA1c concentration (µmol/L) and an absorbance was prepared.

(3) Determination of Total Hemoglobin Concentration in Each Blood Cell Fraction

For each of the samples, centrifugation was carried out at 3,000 rpm (1500×G) at 25° C. for 5 minutes to obtain a blood cell fraction. For each of the blood cell fractions, measurement was carried out by the same method as in (1) by using hemoglobin B-test Wako, and a total hemoglobin concentration (µmol/L) in each of the blood cell fractions was determined based on the obtained measurement value and the calibration curve of (1).

(4) Determination of HbA1c Concentration in Each Blood Cell Fraction

For each of the blood cell fractions obtained in (3), measurement was carried out by the same method as in (2) using the measuring kit 2A of the present invention, and an HbA1c concentration (µmol/L) in each of the blood cell fractions was determined based on the obtained measurement value and the calibration curve of (2).

(5) Determination of HbA1c (%) (=Proportion of HbA1c Concentration to Total Hemoglobin Concentration)

Based on the total hemoglobin concentration (µmol/L) in each of the blood cell fractions determined in the above (3) and the HbA1c concentration (µmol/L) in each of the blood cell fractions determined in the above (4), HbA1c (%) was calculated as an NGSP value (international standard value) by the following Expression (II).

$$\text{HbA1c (\%)} = [\text{HbA1c concentration (µmol/L)}]/[\text{total hemoglobin concentration (µmol/L)}] \times 98.2 + 1.97 \quad (II)$$

(6) Determination of HbA1c (%) in Same Blood Cell Fraction by KO500 Method

Using the same blood cell fraction as the blood cell fraction used for determining HbA1c (%) in the above (5), HbA1c (%) in each blood cell fraction was determined by the KO500 method using HPLC.

(7) Correlation Between Measuring Method of Present Invention and KO500 Method

Based on the HbA1c (%) determined in the above (5) using the measuring method of the present invention and the HbA1c (%) determined in the above (6) using the KO500 method, a correlation between the measuring method of the present invention and the KO500 method was verified, and a correlation coefficient was determined. As a result, the correlation coefficient between both the measurement methods was 0.998 to afford a good correlation between both the measurement methods. Accordingly, it proved that HbA1c in a sample can be accurately measured by the measuring method of the present invention using the kit 2A of Example 3.

(8) Correlation Expression Between HbA1c Concentration and Absorbance ~ Comparison of Sensitivity A slope of a linear function representing a relationship between the HbA1c concentration (x axis) in each of the blood cell fractions determined in the above (4) and the absorbance (y axis) for each of the blood cell fractions was determined, and the slope was used as an index of sensitivity in HbA1c measurement. The slope is an absorbance for HbA1c (1 µmol/L). As a result, the slope was 0.0108.

HbA1c (%) in each of the samples was determined in the same procedure as above except that each kit of the kits 2B, 2C, 2D, 2E, 2F, 2G, 2H, and 2I of Example 3 was used in place of the kit 2A of Example 3, and a correlation between the measuring method using each kit of the kits 2B, 2C, 2D, 2E, 2F, 2G, 2H, and 2I and the KO500 method was verified to afford a correlation coefficient. The results are shown in Table 2.

In addition, in the same procedure as in the above (8) except that each kit of the kits 2B, 2C, 2D, 2E, 2F, 2G, 2H, and 2I of Example 3 was used in place of the kit 2A of Example 3, an absorbance for HbA1c (1 mol/L) was determined in measurement using each of the kits. The results are shown in Table 2.

[0132]

Comparative Example 4

HbA1c (%) in each of the blood cell fractions was determined in the same procedure as in Example 4 except that each kit of the kits 2a, 2b, 2c, 2d, and 2e of Comparative Example 3 was used in place of the kit 2A of Example 3, and a correlation between the measuring method using each of the kits 2a, 2b, 2c, 2d, and 2e and the KO500 method was verified to afford a correlation coefficient. The results are shown in Table 2.

In addition, in measurement using each of the kits 2a, 2b, 2c, and 2d of Comparative Example 3, a slope of a linear function representing a relationship with the absorbance (y-axis) for each of the blood cell fractions was determined, and the slope was used as an index of sensitivity in HbA1c measurement. The slope of the correlation expression is an absorbance per HbA1c (1 µmol/L). The results are shown in Table 2.

TABLE 2

| Kit | Product name (Concentration) | Anionic surfactant Type | Correlation coefficient* | Sensitivity** |
|---|---|---|---|---|
| 2A | NIKKOL LMT (1 g/L) | N-Acyl taurine salt | 0.998 | 0.0108 |
| 2B | NIKKOL PMT (0.5 g/L) | N-Acyl taurine salt | 0.985 | 0.0079 |
| 2C | NIKKOL LSA-F (0.5 g/L) | Alkyl sulfoacetic acid salt | 0.999 | 0.0077 |
| 2D | NIKKOL AKYPO RLM 45 NV (5 g/L) | Polyoxyethylene alkyl ether acetic acid salt | 0.999 | 0.0083 |
| 2E | NIKKOL ALANIATE LN-30 (5 g/L) | N-Acyl amino acid salt | 0.993 | 0.0059 |
| 2F | NIKKOL SARCOSINATE PN (0.5 g/L) | N-Acyl amino acid salt | 0.993 | 0.0099 |
| 2G | PLYSURF AL (5 g/L) | Polyoxyethylene polycyclic phenyl ether phosphoric acid | 0.985 | 0.0055 |
| 2H | PLYSURF A212C (2 g/L) | Polyoxyethylene alkyl ether phosphoric acid | 0.990 | 0.0067 |
| 2I | NIKKOL SLP-N (0.5 g/L) | Alkyl phosphoric acid | 0.970 | 0.0066 |
| 2a | NEOGEN POWDER W (2 g/L) | Linear alkylbenzene sulfonic acid | 0.912 | 0.0025 |
| 2b | NIKKOL SLS (0.5 g/L) | Alkyl sulfate | 0.990 | 0.0020 |
| 2c | NIKKOL OS-14 (1 g/L) | α-Olefin sulfonic acid | 0.994 | 0.0030 |
| 2d | NIKKOL SBL-2N-27 (2.5 g/L) | Polyoxyethylene alkyl ether sulfate | 0.992 | 0.0040 |
| 2e | NONSAL LK-2 (0.25 g/L) | Alkyl metal salt of natural fatty acid | −0.279 | — |

*Correlation coefficient: Correlation coefficient relating to a correlation with the KO500 method
**Sensitivity: A slope of a linear function representing a relationship between an HbA1c concentration (x axis) in each of the blood cell fractions and an absorbance (y axis) for each of the blood cell fractions, which represents an absorbance per HbA1c (1 µmol/L).

As is apparent from Table 2, in measurement using each of the kits 2A to 2I of Example 3 of the present invention as well as measurement using each of the kits 2a to 2d of Comparative Example 3 which comprise the anionic surfactant described in PCT International Publication No. WO2015/060429, a good correlation with the KO500 method was recognized. In a case where the kit 2e was used, glycated hemoglobin could not be measured.

Furthermore, as is apparent from Table 2, the measurement using each of the kits 2A to 2I of Example 3 of the present invention showed a high absorbance per HbA1c concentration (µmol/L) as compared with the measurement using each of the kits 2a to 2d of Comparative Example 3. Accordingly, it proved that the measuring methods of the present invention show a high sensitivity as compared with the measuring methods using each of the kits 2a to 2e of Comparative Example 3, and the measuring methods of the present invention enables a highly sensitive measurement of glycated hemoglobin.

Example 5

Each of the HbA1c measuring kits (kit 2J to 2L) comprising the following first reagent and second reagent were prepared.
First Reagent
Bis-Tris (pH 6.5) 50 mmol/L
DA-67 40 µmol/L
NIKKOL LMT 1.0 g/L
Second Reagent
Phosphate buffer solution (pH 6.5) 10 mmol/L
FPOX-47Δ3 1.5 kU/L
Peroxidase 200 kU/L
Stabilizers J to L (see Table 3)

Example 6

HbA1c (%) in each of the blood cell fractions was determined in the same procedure as in Example 4 except that each of the kits 2J, 2K and 2L of Example 5 was used in addition to the kit 2A of Example 3, and a correlation between the measuring method using each of the kits 2A, 2J, 2K, and 2L and the KO500 method was verified to afford a correlation coefficient. The results are shown in Table 3.

In addition, in measurement using each of the kit 2A of Example 3, and the kits 2J, 2K, and 2L of Example 5, a slope of a linear function representing a relationship with the absorbance (y-axis) for each of the blood cell fractions was determined, and the slope was used as an index of sensitivity in HbA1c measurement. The slope of the correlation expression is an absorbance per HbA1c (1 µmol/L). The results are shown in Table 3.

TABLE 3

| Kit | Stabilizer in second reagent | Correlation coefficient* | Sensitivity** |
|---|---|---|---|
| 2A | Absent | 0.998 | 0.0100 |
| 2J | Glycerin (100 g/L) | 0.990 | 0.0087 |
| 2K | Ethylene glycol (100 g/L) | 0.996 | 0.0093 |
| 2L | Propylene glycol (100 g/L) | 0.996 | 0.0092 |

*Correlation coefficient: Correlation coefficient relating to a correlation with the KO500 method
**Sensitivity: A slope of a linear function representing a relationship between an HbA1c concentration (x axis) in each of the blood cell fractions and an absorbance (y axis) for each of the blood cell fractions, which represents an absorbance per HbA1c (1 µmol/L).

As is apparent from Table 3, in the measurement using each of the kits 2J to 2L of Example 5 of the present invention as well as the measurement using the kit 2A of Example 3 of the present invention, a good correlation with the KO500 method was recognized.

In addition, as is apparent from Table 3, in the measurement using each of the kits 2J to 2L of Example 5 of the present invention as well as the measurement using the kit 2A of Example 3, the absorbance per HbA1c concentration (µmol/L) was 0.008 or more.

Therefore, it proved that the method for measuring glycated hemoglobin of the present invention using an N-acyl taurine salt, which is an anionic surfactant, is an accurate and highly sensitive measuring method in the presence of glycerin or alkylene glycol as a stabilizer.

Example 7

(1) Preparation of Hemolyzed Sample

For a blood cell fraction obtained by centrifuging human blood, measurement was carried out in the same manner as in (1) of Example 2 using hemoglobin B-test Wako, which is a reagent for measuring total hemoglobin, and a total hemoglobin concentration of the blood cell fraction was determined based on the obtained absorbance and the calibration curve prepared in (1) of Example 2 which shows a relationship between a total hemoglobin concentration (μmol/L) and an absorbance. Subsequently, the blood cell fractions with thus determined concentration were diluted with purified water and hemolyzed to prepare each of the hemolyzed samples with total hemoglobin concentrations of 4 mg/mL, 6 mg/mL, and 8 mg/mL (2) Preparation of Calibration Curve for Determination of HbA1c Concentration For two blood cell fractions in which HbA1c concentrations were determined to be 2.98 μmol/L and 6.13 μmol/L by the KO500 method, measurement was carried out using the kit 2A of Example 3 according to the following procedure, and an absorbance for each of the blood cell fractions was measured.

Each of the above-mentioned blood cell fractions (9.6 μL) and the first reagent (120 μL) of the kit 2A of Example 3 were added to a reaction cuvette, a reaction was carried out at 37° C. for 5 minutes (first reaction), and an absorbance (E1) of the reaction solution was measured at a main wavelength of 660 nm and a sub-wavelength of 800 nm. Subsequently, the second reagent (40 μL) of the kit 2A of Example 3 was added to the reaction solution, a further reaction was allowed to occur at 37° C. for 5 minutes (second reaction), and an absorbance (E2) of the reaction solution was measured at a main wavelength of 660 nm and a sub-wavelength of 800 nm. E1 was subtracted from E2 to calculate an absorbance difference $\Delta E'2A$, which was taken as an absorbance for each of the blood cell fractions. An absorbance difference $\Delta E'_{physiological\ saline}$ was calculated by the same method except that a physiological saline was used in place of each of the above-mentioned blood cell fractions, and this was taken as an absorbance for the physiological saline. A value calculated by subtracting the absorbance for the physiological saline from the absorbance for each of the blood cell fractions was taken as a blank-corrected absorbance for the blood cell fraction. Based on the blank-corrected absorbance for the blood cell fraction and a blank-corrected absorbance (0 Abs) for the physiological saline, a calibration curve showing a relationship between an HbA1c concentration (μmol/L) and an absorbance was prepared.

(3) Determination of HbA1c Concentration in Each Hemolyzed Sample

For each of the hemolyzed samples prepared in (1), measurement was carried out using the kit 2A of Example 3 by the same method as in (2), and an HbA1c concentration (μmol/L) in each of the hemolyzed samples was determined based on the obtained measurement value and the calibration curve of (2).

(4) Determination of HbA1c (%) (=Proportion of HbA1c Concentration to Total Hemoglobin Concentration)

Based on the total hemoglobin concentration (μmol/L) in each of the hemolyzed samples prepared in the above (1) and the HbA1c concentration (μmol/L) in each of the hemolyzed samples measured in the above (3), HbA1c (%) was calculated as an NGSP value (international standard value) by the following Expression (II).

HbA1c (%)=[HbA1c concentration (μmol/L)]/[total hemoglobin concentration (μmol/L)]×98.2+1.97   (II)

(5) Evaluation of Influence of Total Hemoglobin Concentration

An HbA1c concentration (%) in a hemolyzed sample having a total hemoglobin concentration of 6 mg/mL was taken as a reference 0, and a difference [ΔHbA1c concentration (%)] of HbA1c concentration (%) in each of the hemolyzed samples from the reference was calculated. The results are shown in Table 4.

Similar measurement was carried out using each of the kits 2B to 2I of Example 3 in place of the kit 2A of Example 3 as a kit for measuring HbA1c, and an HbA1c concentration (%) in each of the hemolyzed samples was measured for each of the kits. An HbA1c concentration (%) in a hemolyzed sample having a total hemoglobin concentration of 6 mg/mL was taken as a reference 0, and a difference [ΔHbA1c concentration (%)] of HbA1c concentration (%) in each of the hemolyzed samples from the reference was calculated. The results are shown in Table 4.

Comparative Example 5

By the same method as in Example 7 except that each of the kits 2b to 2d of Comparative Example 3 was used in place of the kit 2A of Example 3, an HbA1c concentration (%) in each of the hemolyzed samples was measured for each of the kits. An HbA1c concentration (%) in a hemolyzed sample having a total hemoglobin concentration of 6 mg/mL was taken as a reference 0, and a difference [ΔHbA1c concentration (%)] of HbA1c concentration (%) in each of the hemolyzed samples from the reference was calculated. The results are shown in Table 4.

TABLE 4

| Kit | Anionic surfactant | ΔHbA1c concentration (%) Sample [hemoglobin concentration (mg/mL)] | | |
|---|---|---|---|---|
| | | 4 | 6 | 8 |
| 2A | NIKKOL LMT | 0.7 | 0.0 | −0.7 |
| 2B | NIKKOL PMT | −1.5 | 0.0 | −0.2 |
| 2C | NIKKOL LSA-F | −0.6 | 0.0 | −0.1 |
| 2D | NIKKOL AKYPO RLM 45 NV | 0.4 | 0.0 | 0.2 |
| 2E | NIKKOL ALANIATE LN-30 | −1.0 | 0.0 | 0.3 |
| 2F | NIKKOL SARCOSINATE PN | 0.8 | 0.0 | −0.1 |
| 2G | PLYSURF AL | 0.3 | 0.0 | −0.8 |
| 2b | NIKKOL SLS | 3.7 | 0.0 | 1.2 |
| 2c | NIKKOL OS-14 | −0.4 | 0.0 | 2.9 |
| 2d | NIKKOL SBL-2N-27 | 1.2 | 0.0 | 2.0 |

As described above, since the hemolyzed sample used for the measurement was prepared from the same human blood, a proportion (%) of HbA1c to total hemoglobin is constant regardless of a total hemoglobin concentration. Accordingly, the fact that the ΔHbA1c concentration (%) is closer to 0 indicates that it is less influenced by the total hemoglobin concentration. As is apparent from Table 4, it was proven that the method for measuring glycated hemoglobin of the present invention using each of the kits 2A to 2G of the present invention is not influenced by the total hemoglobin concentration as compared with the method for measuring glycated hemoglobin using each of the kits 2b to 2d of Comparative Example 3.

Comparative Example 6

Each of the kits for measuring HbA1c (kits 2f to 2m) comprising the following first reagent and second reagent were prepared.
First Reagent
Bis-Tris (pH 6.5) 50 mmol/L
DA-67 40 μmol/L
Surfactants f to m (see Table 5)
Second Reagent
Phosphate buffer solution (pH 6.5) 10 mmol/L
FPDX-47Δ3 1.5 kU/L
Peroxidase 200 kU/L The surfactants f to m are the nonionic surfactants or cationic surfactants described in PCT International Publication No. WO2015/060429. Each of the kits (kits 2f to 2m) of Comparative Example 6 are the same as each of the kits (kits 2a to 2e) of Comparative Example 3 except for the surfactant in the first reagent.

Example 8

Using the kit 2A of Example 3 as a kit for measuring HbA1c, and 6 concentrations of whole blood in which HbA1c concentrations were determined to be 4.9%, 5.6%, 6.7%, 7.5%, 8.4%, and 9.9%, respectively, by the KO500 method, which is an HPLC method, as samples, a correlation coefficient relating to a correlation with the KO500 method and an absorbance per HbA1c (1 μmol/L) as an index of sensitivity were determined in the same procedure as in Example 4. The results are shown in Table 5.

Comparative Example 7

Using each of the kits 2f to 2m of Comparative Example 6 as a kit for measuring HbA1c, and 6 concentrations of whole blood in which HbA1c concentrations were determined to be 4.9%, 5.6%, 6.7%, 7.5%, 8.4%, and 9.9%, respectively, by the KO500 method, which is an HPLC method, as samples, a correlation coefficient relating to a correlation with the KO500 method and an absorbance per HbA1c (1 μmol/L) as an index of sensitivity were determined in the same procedure as in Example 4. The results are shown in Table 5.

TABLE 5

| Kit | Surfactant (concentration) | Correlation coefficient* | Sensitivity** |
|---|---|---|---|
| 2A | NIKKOL LMT (1 g/L) | 0.999 | 0.0091 |
| 2f | C14 TMA (1 g/L) | — | — |
| 2g | C16 TMA (1 g/L) | — | — |
| 2h | Brij 58 (16 g/L) | 0.795 | 0.0006 |
| 2i | n-Dodecyl-β-maltoside (16 g/L) | 0.915 | 0.0006 |
| 2j | Brij58 (16 g/L), C14 TMA (1 g/L) | 0.613 | 0.0002 |
| 2k | Brij58 (16 g/L), C16 TMA (1 g/L) | 0.599 | 0.0004 |

TABLE 5-continued

| Kit | Surfactant (concentration) | Correlation coefficient* | Sensitivity** |
|---|---|---|---|
| 2l | n-Dodecyl-β-maltoside (16 g/L) C14 TMA (1 g/L) | 0.515 | 0.0003 |
| 2m | n-Dodecyl-β-maltoside (16 g/L) C16 TMA (1 g/L) | 0.886 | 0.0006 |

*Correlation coefficient: Correlation coefficient relating to a correlation with the KO500 method
**Sensitivity: A slope of a linear function representing a relationship between an HbA1c concentration (x axis) in each of the blood cell fractions and an absorbance (y axis) for each of the blood cell fractions, which represents an absorbance per HbA1c (1 μmol/L).

As is apparent from Table 5, in the measurement using the kit 2A of Example 3 of the present invention, a good correlation with the KO500 method was recognized, as compared with the measurement using each of the kits 2f to 2m of Comparative Example 6. In particular, in the kits 2f and 2g containing C14 TMA and C16 TMA, respectively, which are cationic surfactants, glycated hemoglobin in the sample could not be measured.

In addition, as is apparent from Table 5, in the measurement using the kit 2A of Example 3 of the present invention, a high absorbance per HbA1c concentration (μmol/L) was exhibited as compared with the measurement using each of the kits 2f to 2m of Comparative Example 6. Accordingly, it proved that the measuring methods of the present invention show a high sensitivity as compared with the measuring methods using each of the kits 2f to 2m of Comparative Example 6, and the measuring methods of the present invention enables a highly sensitive measurement of glycated hemoglobin.

Example 9

A kit (kit 3A) for measuring HbA1c which comprises the following first reagent comprising an enzyme that catalyzes a reaction of oxidizing glycated hemoglobin to generate hydrogen peroxide and second reagent comprising an N-acyl taurine salt, which is an anionic surfactant, was prepared.
First Reagent
Bis-Tris (pH 7.0) 50 mmol/L
DA-67 40 μmol/L
FPDX-47Δ3 0.6 kU/L
Second Reagent
Bis-Tris (pH 7.0) 50 mmol/L
Sodium azide 0.1 g/L
NIKKOL LMT 4.5 g/L
Peroxidase 200 kU/L Example 10

Using the kit 3A of Example 9 as a kit for measuring HbA1c, and 5 concentrations of whole blood in which HbA1c concentrations were determined to be 3.7%, 4.4%, 5.4%, 6.7%, and 9.2%, respectively, by the KO500 method, which is an HPLC method, as samples, a proportion [HbA1c (%)] of HbA1c concentration (amount) to total hemoglobin concentration (amount) in each of the samples was determined by the following procedure.

(1) Preparation of Calibration Curve for Determination of Total Hemoglobin Concentration Using hemoglobin B-test Wako, which is a kit for measuring total hemoglobin (SLS-hemoglobin method) (manufactured by Wako Pure Chemical Industries, Ltd.), measurement was carried out in the same manner as in (1) of Example 2, and a calibration curve showing a relationship between a total hemoglobin concentration and an absorbance was prepared.

(2) Preparation of Calibration Curve for Determination of HbA1c Concentration

For two blood cell fractions in which HbA1c concentrations were determined to be 3.64 μmol/L and 9.18 μmol/L by the KO500 method, measurement was carried out in the same manner as in (2) of Example 7 using the HbA1c measuring kit 3A of Example 9, and an absorbance for each of the blood cell fractions was measured. Similarly, measurement was carried out using a physiological saline in place of the blood cell fraction, and an absorbance for the physiological saline was measured. The absorbance for the physiological saline was subtracted from the absorbance for each of the blood cell fractions to afford a blank-corrected absorbance for the blood cell fraction. Based on the blank-corrected absorbance for the blood cell fraction and a blank-corrected absorbance (0 Abs) for the physiological saline, a calibration curve showing a relationship between an HbA1c concentration (mol/L) and an absorbance was prepared.

(3) Determination of Total Hemoglobin Concentration in Each Blood Cell Fraction

For each of the samples, centrifugation was carried out at 3,000 rpm (1500×G) at 25° C. for 5 minutes to obtain a blood cell fraction. For each of the blood cell fractions, measurement was carried out by the same method as in (1) by using hemoglobin B-test Wako, and a total hemoglobin concentration (μmol/L) in each of the blood cell fractions was determined based on the obtained measurement value and the calibration curve of (1).

(4) Determination of HbA1c Concentration in Each Blood Cell Fraction

For each of the blood cell fractions obtained in (3), measurement was carried out by the same method as in (2) using the measuring kit 3A of the present invention, and an HbA1c concentration (μmol/L) in each of the blood cell fractions was determined based on the obtained measurement value and the calibration curve of (2).

(5) Determination of HbA1c (%) (=Proportion of HbA1c Concentration to Total Hemoglobin Concentration)

Based on the total hemoglobin concentration (μmol/L) in each of the blood cell fractions determined in the above (3) and the HbA1c concentration (μmol/L) in each of the blood cell fractions determined in the above (4), HbA1c (%) was calculated as an NGSP value (international standard value) by the following Expression (II).

$$\text{HbA1c (\%)} = [\text{HbA1c concentration (μmol/L)}]/[\text{total hemoglobin concentration (μmol/L)}] \times 98.2 + 1.97 \quad \text{(II)}$$

(6) Determination of HbA1c (%) in Same Blood Cell Fraction by KO500 Method

Using the same blood cell fraction as the blood cell fraction used for determining HbA1c (%) in the above (5), HbA1c (%) in each of the blood cell fractions was determined by the KO500 method, which is an HPLC method.

(7) Correlation Between Measuring Method of Present Invention and KO500 Method

Based on the HbA1c (%) determined in the above (5) using the measuring method of the present invention and the HbA1c (%) determined in the above (6) using the KO500 method, a correlation between the measuring method of the present invention and the KO500 method was verified to determine a correlation coefficient. As a result, the correlation coefficient between both the measurement methods was 0.974, and a good correlation was recognized between both the measurement methods.

(8) Comparison of Sensitivity

A slope of a linear function representing a relationship between the HbA1c concentration (x axis) in each of the blood cell fractions determined in the above (4) and the absorbance (y axis) for each of the blood cell fractions was determined, and the slope was used as an index of sensitivity in HbA1c measurement. The slope is an absorbance for HbA1c (1 μmol/L). As a result, the slope was 0.0058.

Therefore, it proved that the method for measuring glycated hemoglobin of the present invention using a kit for measuring glycated hemoglobin of the present invention which comprises a first reagent comprising an enzyme that catalyzes a reaction of oxidizing glycated hemoglobin to generate hydrogen peroxide, and a second reagent comprising an N-acyl taurine salt, which is an anionic surfactant, is an accurate and highly sensitive measuring method.

INDUSTRIAL APPLICABILITY

According to the present invention, a method, a reagent, and a kit are provided for measuring glycated hemoglobin in a hemoglobin-containing sample useful for diagnosis of diabetes and the like.

The invention claimed is:

1. A method for measuring glycated hemoglobin in a hemoglobin-containing sample, comprising:

reacting glycated hemoglobin in the hemoglobin-containing sample with an enzyme that catalyzes a reaction of oxidizing the glycated hemoglobin to generate hydrogen peroxide, in the presence of at least one anionic surfactant selected from the group consisting of N-acyl taurine in which a hydrogen atom of the amino group is optionally substituted with a substituent, alkyl sulfoacetic acid, polyoxyethylene alkyl ether acetic acid, N-acyl amino acid in which a hydrogen atom of the amino group is optionally substituted with a substituent, polyoxyethylene alkyl ether phosphoric acid, polyoxyethylene polycyclic phenyl ether phosphoric acid, alkyl phosphoric acid, and salts thereof; and measuring the generated hydrogen peroxide.

2. The method according to claim 1, wherein the measurement of the hydrogen peroxide is carried out with a reagent for measuring hydrogen peroxide.

3. The method according to claim 2, wherein the reagent for measuring hydrogen peroxide is a reagent containing a peroxidase and a leuco-type chromogen.

4. The method according to claim 3, wherein the leuco-type chromogen is a phenothiazine-based chromogen.

5. The method according to claim 4, wherein the phenothiazine-based chromogen is 10-(carboxymethylaminocarbonyl)-3,7-bis(dimethylamino)phenothiazine or a salt thereof.

6. The method according to claim 1, wherein the method comprises reacting the glycated hemoglobin in the hemoglobin-containing sample with at least one anionic surfactant selected from the group consisting of N-acyl taurine in which a hydrogen atom of the amino group may be substituted with a substituent, alkyl sulfoacetic acid, polyoxyethylene alkyl ether acetic acid, N-acyl amino acid in which a hydrogen atom of the amino group may be substituted with a substituent, polyoxyethylene alkyl ether phosphoric acid, polyoxyethylene polycyclic phenyl ether phosphoric acid, alkyl phosphoric acid, and salts thereof, then adding the enzyme that catalyzes a reaction of oxidizing the glycated hemoglobin, and reacting the glycated hemoglobin in the hemoglobin-containing sample with the enzyme that catalyzes a reaction of oxidizing the glycated hemoglobin to generate hydrogen peroxide, in the presence of the at least one anionic surfactant selected from the group consisting of N-acyl taurine in which a hydrogen atom of the amino group may be substituted with a substituent, alkyl sulfoacetic acid, polyoxyethylene alkyl ether acetic acid, N-acyl amino acid in which a hydrogen atom of the amino group may be substituted with a substituent, polyoxyethylene alkyl ether phosphoric acid, polyoxyethylene polycyclic phenyl ether phosphoric acid, alkyl phosphoric acid, and salts thereof.

7. The method according to claim 1, wherein the at least one anionic surfactant comprises at least one surfactant selected from the group consisting of N-acyl taurine in which a hydrogen atom of the amino group is optionally substituted with a substituent, alkyl sulfoacetic acid, polyoxyethylene alkyl ether acetic acid, polyoxyethylene alkyl ether phosphoric acid, polyoxyethylene polycyclic phenyl ether phosphoric acid, alkyl phosphoric acid, and salts thereof.

* * * * *